United States Patent [19]
Hudkins et al.

[11] Patent Number: 5,808,060
[45] Date of Patent: Sep. 15, 1998

[54] FUSED ISOINDOLONES

[75] Inventors: Robert L. Hudkins, Chester Springs; Neil W. Johnson, Downingtown, both of Pa.

[73] Assignee: Cephalon, Inc., West Chester, Pa.

[21] Appl. No.: 761,951

[22] Filed: Dec. 9, 1996

Related U.S. Application Data

[60] Provisional application No. 60/008,733, Dec. 11, 1995.

[51] Int. Cl.⁶ ...................... C07D 487/00; C07D 487/02; C07D 487/04; C07D 495/04
[52] U.S. Cl. .......................... 540/577; 540/578; 544/184; 544/233; 544/245; 544/338; 546/41; 548/416; 548/417
[58] Field of Search .................................... 548/416, 417; 540/577, 578; 544/184, 233, 245, 338; 546/41

[56] References Cited

U.S. PATENT DOCUMENTS

| | | | |
|---|---|---|---|
| 4,735,939 | 4/1988 | McCoy et al. | 514/211 |
| 4,816,450 | 3/1989 | Bell et al. | 514/25 |
| 4,877,776 | 10/1989 | Murakata et al. | 514/43 |
| 4,923,986 | 5/1990 | Murkata et al. | 540/545 |
| 5,106,864 | 4/1992 | Suda et al. | 514/410 |
| 5,438,050 | 8/1995 | Kleinschroth et al. | 514/183 |
| 5,468,872 | 11/1995 | Glicksman et al. | 548/416 |
| 5,475,110 | 12/1995 | Hudkins et al. | 546/256 |
| 5,489,608 | 2/1996 | Kleinschroth et al. | 514/410 |
| 5,516,771 | 5/1996 | Dionne et al. | 514/211 |
| 5,547,976 | 8/1996 | Slater et al. | 514/410 |
| 5,591,842 | 1/1997 | Kojiri et al. | 536/26.1 |
| 5,591,855 | 1/1997 | Hudkins et al. | 546/256 |
| 5,594,009 | 1/1997 | Hudkins et al. | 514/338 |
| 5,618,809 | 4/1997 | Barrabee et al. | 514/211 |
| 5,654,427 | 8/1997 | Dionne et al. | 540/545 |

FOREIGN PATENT DOCUMENTS

| | | |
|---|---|---|
| 0 238 011 | 9/1987 | European Pat. Off. |
| 0 558 962 | 9/1993 | European Pat. Off. |
| 4217963 | 12/1993 | Germany. |
| WO 94/02488 | 2/1994 | WIPO. |
| WO 96/11933 | 4/1996 | WIPO. |

OTHER PUBLICATIONS

Davis et al., "A Mild Conversion of Maleic Anhydrides into Maleimides," *Tetrahedron Letters*, 31(36):5201–5204, 1990.

Eldin et al., "Structural Effects on the Rates of Formation and the Stability of Enols of Cyclic Benzyl Ketones," *J. Am. Chem. Soc.*, 113:1344–1349, 1991.

Glassco et al., "Synthesis, Optical Resolution, Absolute Configuration, and Preliminary Pharmacology of (+)–and (–)–cis–2,3,3a,4,5,9b–Hexahydro–1–methyl–1H–pyrrolo–[3,2–h] isoquinoline, a Structural Analog of Nicotine," *J. Med. Chem.*, 36:3381–3385, 1993.

Glicksman et al., "K–252a and Staurosporine Promote Choline Acetyltransferase Activity in Rat Spinal Cord Cultures," *J. Neurochemistry*, 61(1):210–221, 1993.

Kase et al., "K–252a, a Potent Inhibitor of Protein Kinase C from Microbial Origin," *J. Antibiotics*, 39(8):1059–1065, 1986.

Kikkawa et al., "Calcium–activated, Phospholipid–dependent Protein Kinase from Rat Brain," *J. Biol. Chem.*, 257(22):13341–13348, 1982.

Krustoš´ková et al., "Addition and Cycloaddition Reactions of Furo[3,2–b]—Pyrroles and their Benzo [b] Analogues: an NMR Study of Structure of Products," *Czechoslovak Chemical Commun.*, 53:1770–1778, 1988.

Kumar et al., "Synthesis of Thieno[2,3–b] pyrroles," *Indian J. of Chem.*, 20B:271–274, 1981.

Moody et al., "Synthesis of the Staurosporine Aglycon," *J. Org. Chem.*, 57:2105–2114, 1992.

Phelps et al., "Generation Patterns of Four Groups of Cholinergic Neurons in Rat Cervical Spinal Cord: A Combined Tritiated Thymidine Autoradiographic and Choline Acetyltransferase Immunocytochemical Study," *J. Comparative Neurology*, 273:459–472, 1988.

Reinecke et al., "Thermolysis of Thiophenedicarboxylic Acid Anhydrides as a Route to Five–Membered Hetarynes," *J. Am. Chem. Soc.*, 103:2760–2769, 1981.

Skramstad, "Cyclopenta–thiophenes, Part III: (Cyclopenta [b] thiophenes from the Reaction Between 2,3–Diformylthiophene and Nitromethane," *Acta Chemica Scandinavica*, 25:1287–1296, 1971.

Smith et al., "Trophic Effects of Skeletal Muscle Extracts on Ventral Spinal Cord Neurons In Vitro: Separation of a Protein with Morphologic Activity from Proteins with Cholinergic Activity," *J. Cell Biol.*, 101:1608–1621, 1985.

Soth et al., "Recherches en série hétérocyclique No. 14: Sur des voies d'accés á des thiéno, sélénolo, furo et pyrrolopyrroles," *Canadian J. Chem.*, 56(7):1429–1434, 1978.

Taoka et al., "Induction of Differentiation of HL–60 Cells by Protein Kinase C Inhibitor, K252a," *Biomed. and Biophys. Research Commun.*, 170(3):1151–1156, 1990.

Thies et al., "Ring–Size Effects in the Reaction of Benzochycloalkadiene Epoxides with Lithium Diisopropylamide," *J. Org. Chem.*, 44(8):1342–1344, 1979.

Wood et al., "Total Synthesis of (+)–and (–)–K252a," *J. Am. Chem.*, 117(41):10413–10414, 1995.

*Primary Examiner*—Mukund J. Shah
*Assistant Examiner*—Deepak R. Rao
*Attorney, Agent, or Firm*—Fish & Richardson P.C.

[57] ABSTRACT

Disclosed are biologically active, non-indole-containing compounds referred to as fused isoindolones, which are represented by the following general formula:

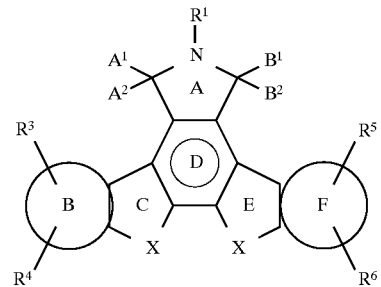

The fused indolones can be obtained by complete chemical synthesis. Methods for making and using the fused isoindolones are disclosed.

18 Claims, 15 Drawing Sheets

FUSED ISOINDOLONES

CROSS REFERENCE TO RELATED APPLICATIONS

This application claims benefit of U.S. Provisional application Ser. No. 60/008,733, filed Dec. 11, 1995.

FIELD OF THE INVENTION

The invention relates to fused aryl and heteroaryl fused isoindol-2- and -2,4-diones, which are referred to herein as "fused isoindolones". The invention also relates to methods for making these compounds, and methods for using the compounds.

BACKGROUND OF THE INVENTION

Publications cited herein are incorporated by reference.

The microbial-derived material referred to as "K-252a" has gained significant attention over the past several years due to the variety of functional activities which it possesses. K-252a is an indolocarbazole alkaloid that was originally isolated from a *Nocordiosis sp.* culture (Kase, H et al. 39 *J. Antibiotics* 1059, 1986). K-252a is an inhibitor of several enzymes, including protein kinase C ("PKC") and trk tyrosine kinase. The reported functional activities of K-252a are numerous and diverse, e.g., tumor inhibition (U.S. Pat. Nos. 4,877,776 and 5,063,330; European Publication 238, 011 in the name of Nomato); anti-insecticidal activity (U.S. Pat. No. 4,735,939); inhibition of inflammation (U.S. Pat. No. 4,816,450); treatment of diseases associated with neuronal cells (WIPO Publication WO 94/02488, published Feb. 3, 1994 in the names of Cephalon, Inc. and Kyowa Hakko Kogyo Co., Ltd.).

The reported indolocarbozoles share several common attributes. In particular, each comprises a bis-indole heterocyclic moiety. Staurosporine (derived from Streptomyces sp.) and K-252a (derived from Nocordiosis sp.) each further comprise a sugar moiety linked via two N-glycosidic bonds (attached to the indole nitrogens). Both K-252a and staurosporine have been extensively studied with respect to their utility as therapeutic agents. The indolocarbozoles are generally lyophilic, which allows for their comparative ease in crossing biological membranes, and, unlike proteinaceous materials, they manifest a longer in vivo half life.

While K-252a possesses such varied and useful activities, a drawback to the compound is that because it is of microbial origin, it must be derived from culture media via a fermentation process. The total synthesis of K-252a has been recently reported in the literature, but the synthesis is not practical for commercial use (Wood, J. et al. *J. Am. Chem. Soc*, 1995, 117, 10413.). Accordingly, compounds that possess desired functional activities of K-252a but which can be readily obtained using chemical synthesis techniques would offer distinct advantages over the indolocarbazole compounds currently available.

SUMMARY OF THE INVENTION

The invention features compounds referred to herein as "fused isoindolones." These compounds are biologically active. The fused isoindolones are non-indole-containing molecules that can be chemically synthesized de novo.

The fused isoindolones of this invention are different from indolocarbazoles in that they do not include a nitrogen at the 12- or 13-positions (the alphabetical ring designations set forth in Porter et al., 57 *J. Org. Chem.* 2105, 1992, are utilized for reference purposes). Additionally, the fused isoindolones do not include a sugar moiety linked via two N-glycoside bonds. Because these compounds do not include such a sugar moiety, synthetic production can be readily achieved. Beneficially and surprisingly, these non-indole-containing compounds, which are not of microbial origin, can be readily synthesized, and they possess biological activities that allow for a broad range of applications heretofore only observed with certain indolocarbozoles.

Fused isoindolones of the invention are represented by the following general formula (Formula I):

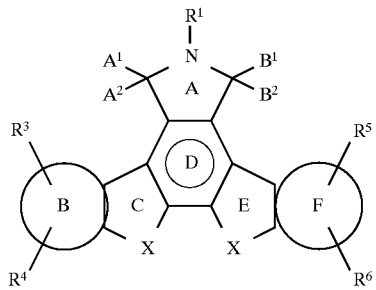

Preferred fused isoindolones are represented by Formula II:

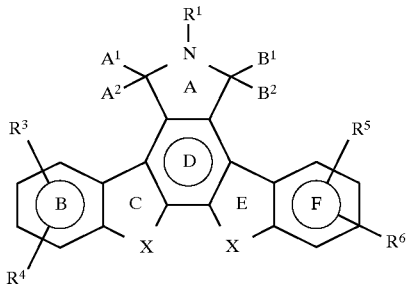

Constituent members are described in detail, below. In both Formula I and Formula II, in the C and E rings, constituent "X" is not nitrogen.

Preferred routes of synthesis are also described herein, including methodologies for the preparation of lactam isomers.

The fused isoindolones can be used in a variety of ways, e.g., enhancing the function and/or survival of cells of neuronal lineage, either singularly or in combination with neurotrophic factor(s) and/or indolocarbozoles; inhibition of protein kinase C (PKC); and inhibition of trk tyrosine kinase activity. The latter activity indicates utility for inhibition of proliferation of cancer cells include cancerous conditions of the prostate. Because of these varied activities, the compounds of this invention find utility in a variety of settings, including research and therapeutic environments.

DETAILED DESCRIPTION

I. Brief Description of the Drawings FIG. 1 is a graph evidencing the effect of fused isoindolone derivatives I-1 and I-2 on spinal cord ChAT activity.

II. Fused Isoindolones

Figure 1:
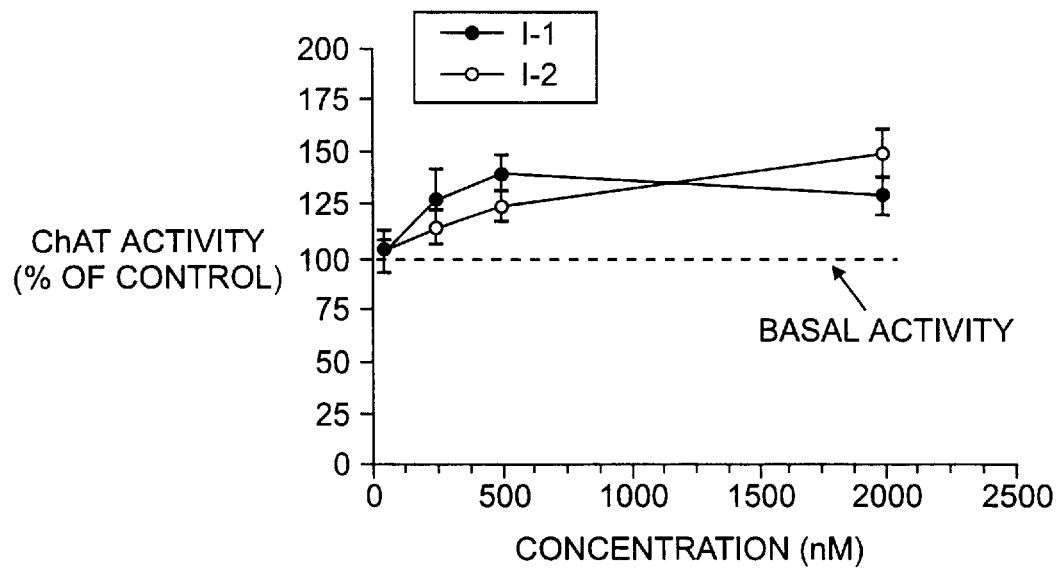

The invention features fused isoindolones represented by Formula I:

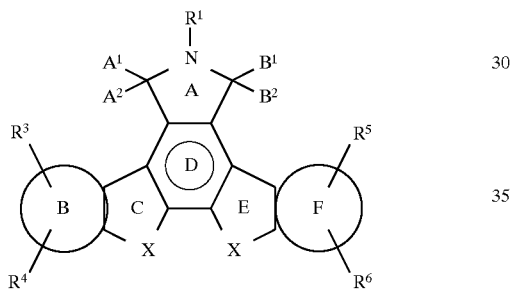

wherein:
ring B and ring F are independently selected from the group consisting of:
  (a) a 6-membered carbocyclic aromatic ring in which up to 3 carbon atoms are replaced by nitrogen atoms;
  (b) a 5-membered carbocyclic aromatic ring; and
  (c) a 5-membered carbocyclic aromatic ring in which:
     (1) one carbon atom is replaced by an oxygen, nitrogen, or sulfur atom; or
     (2) two carbon atoms are replaced by a nitrogen and a sulfur atom, or a nitrogen and an oxygen atom;
$R^1$ is selected from the group consisting of H; alkyl of 1–4 carbons; aryl; arylalkyl; heteroaryl; heteroarylalkyl; $COR^9$, where $R^9$ is selected from the group consisting of alkyl of 1–4 carbons, aryl and heteroaryl; $—OR^{10}$, where $R^{10}$ is selected from the group consisting of H and alkyl of 1–4 carbons; $—CONH_2$, $—NR^7R^8$, $—(CH_2)_nNR^7R^8$, and $—O(CH_2)_nNR^7R^8$, where n is 1–4, and
  (a) $R^7$ and $R^8$ independently are selected from the group consisting of H and alkyl of 1–4 carbons; or
  (b) $R^7$ and $R^8$ together form a linking group of the formula $—(CH_2)_2—X^1—(CH_2)_2—$,
where $X^1$ is selected from the group consisting of $—O—$, $—S—$, and $—CH_2—$;
$A^1$ and $A^2$, pairwise, are selected from the group consisting of: H, H; H, $—OR^{11}$, where $R^{11}$ is H, alkyl of 1–4 carbons, aryl of 6–10 carbons, or heteroaryl; H, $—SR^{11}$; H, $—N(R^{11})_2$; =O; =S; and =$NR^{11}$, where $A^1$ and $A^2$ together can represent a double-bonded atom;

$B^1$ and $B^2$, pairwise, are selected from the group consisting of: H, H; H, $—OR^{11}$; H, $—SR^{11}$; H, $—N(R^{11})_2$; =O; =S; and =$NR^{11}$, where $B^1$ and $B^2$ together can represent a double-bonded atom; with the proviso that at least one of the pairs $A^1$ and $A^2$, and $B^1$ and $B^2$ is =O;

X, at each position, is independently selected from the group consisting of:
  (a) an unsubstituted alkylene of 1–3 carbons;
  (b) an alkylene of 1–3 carbons substituted with $R^2$, where $R^2$ is selected from the group consisting of:
     (1) $OR^{10}$; $—SR^{10}$; $R^{15}$, where $R^{15}$ is alkyl of 1–4 carbons; phenyl; naphthyl; arylalkyl of 7–15 carbons; H; $—SO_2R^9$; $—CO_2R^9$; $—COR^9$; alkyl, alkenyl, and alkynyl of 1–8 carbons, where
        (i) each alkyl, alkenyl, or alkynyl of 1–8 carbons is unsubstituted; or
        (ii) each alkyl, alkenyl, or alkynyl of 1–8 carbons is substituted with a substituent selected from the group consisting of 1–3 aryl of 6–10 carbons; heteroaryl; F; Cl; Br; I; $—CN$; $—NO_2$; OH; $—OR^9$; $—O(CH_2)_nNR^7R^8$, where n is 1–4; $—OCOR^9$; $—OCONHR^9$; O-tetrahydropyranyl; $NH_2$; $—NR^7R^8$; $—NR^{10}COR^9$; $—NR^{10}CO_2R^9$; $—NR^{10}CONR^7R^8$; $—NHC(=NH)NH_2$; $—NR^{10}SO_2R^9$; $—S(O)_yR^{11}$, where y is 1 or 2; $—SR^{11}$; $—CO_2R^9$; $—CONR^7R^8$; $—CHO$; $COR^9$; $—CH_2OR^7$; $—CH=NNR^{11}R^{12}$, where $R^{12}$ is selected from the group consisting of H, alkyl of 1–4 carbons, aryl of 6–10 carbons, and heteroaryl; $—CH=NOR^{11}$; $—CH=NR^9$; $—CH=NNHCH(N=NH)NH_2$; $—SO_2NR^{12}R^{13}$, where $R^{13}$ is selected from the group consisting of H, alkyl of 1–4 carbons, aryl of 6–10 carbons, and heteroaryl, or $R^{12}$ and $R^{13}$ together form a linking group; $—PO(OR^{11})_2$, $—OR^{14}$, where $R^{14}$ is the residue of an amino acid after the hydroxyl group of the carboxyl group is removed; or
     (2) a monosaccharide of 5–7 carbons, where each hydroxyl group of the monosaccharide independently is either unsubstituted or is replaced by H, alkyl of 1–4 carbons, alkylcarbonyloxy of 2–5 carbons or alkoxy of 1–4 carbons; and
  (c) a functional group selected from the group consisting of $—CH=CH—$; $—CHOH—CHOH—$; $—O—$; $—S—$; $—S(=O)—$; $—S(S=O)_2—$; $—C(R^{10})_2—$; $—C=C(R^2)_2$; $—C(=O)—$; $—C(=NOR^{11})—$; $—C(OR^{11})(R^{11})—$; $—C(=O)CH(R^{15})—$; $—CH(R^{15})C(=O)—$; $—C(=NOR^{11})CH(R^{15})—$; $—CH(R^{15})C(=NOR^{11})—$; $CONR^{15}$; $NR^{15}CO$; $—CH_2Z—$; $—ZCH_2—$; $—CH_2ZCH_2—$, where Z is $—CR^{11}$; $—O—$; $—S—$; $—C(=O)OR^{11}$; $—C(=NOR^{11})$; and $—NR^{11}$;

$R^3$, $R^4$, $R^5$ and $R^6$ each is independently selected from the group consisting of: H; aryl; heteroaryl; F; Cl; Br; I; $—CN$; $CF_3$; $—NO_2$; OH; $—OR^9$; $—O(CH_2)_nNR^7R^8$; $—OCOR^9$; $—OCONHR^9$; $NH_2$; $—CH_2OH$; $—CH_2OR^{14}$; $—NR^7R^8$; $—NR^{10}COR^9$; $—NR^{10}CONR^7R^8$; $—SR^{11}$; $—S(O)_yR^{11}$, where y is 1 or 2; $—CO_2R^9$; $—COR^9$; $—CONR^7R^8$; $—CHO$; $—CH=NOR^{11}$; $—CH=NR^9$; $—CH=NNR^{11}R^{12}$;

—$(CH_2)_nSR^9$, where n is 1–4; —$(CH_2)_nS(O)_yR^9$; —$CH_2SR^{15}$, where $R^{15}$ is alkyl of 1–4 carbons; —$CH_2S(O)_yR^{14}$; —$(CH_2)_nNR^7R^8$; —$(CH_2)_nNHR^{14}$; alkyl, alkenyl, alkynyl of 1–8 carbons, where (a) each alkyl, alkenyl, or alkynyl of 1–8 carbons is unsubstituted; or (b) each alkyl, alkenyl, or alkynyl of 1–8 carbons is substituted with 1–3 aryl of 6–10 carbons; heteroaryl; F; Cl; Br; I; —CN; —$NO_2$; OH; —$OR^9$; —$O(CH_2)_nNR^7R^8$; —$OCOR^9$; —OCONHR$^9$; O-tetrahydropyranyl; $NH_2$; —$NR^7R^8$; —$NR^{10}COR^9$; —$NR^{10}CO_2R^9$; —$NR^{10}CONR^7R^8$; —NHC(=NH)$NH_2$; —$NR^{10}SO_2R^9$; —$S(O)_yR^{11}$, where y is 1 or 2; —$SR^{11}$; —$CO_2R^9$; —$CONR^7R^8$; —CHO; $COR^9$; —$CH_2OR^7$; —CH=$NNR^{11}R^{12}$; —CH=$NOR^{11}$; —CH=$NR^9$; —CH=NNHCH (N=NH)$NH_2$; —$SO_2NR^{12}R^{13}$; —PO($OR^{11}$)$_2$; $OR^{14}$; or a monosaccharide of 5–7 carbons where each hydroxyl group of the monosaccharide independently is either unsubstituted or is replaced by H, alkyl of 1–4 carbons, alkylcarbonyloxy of 2–5 carbons or alkoxy of 1–4 carbons.

Preferred embodiments of the invention are fused isoindolones represented by Formula II:

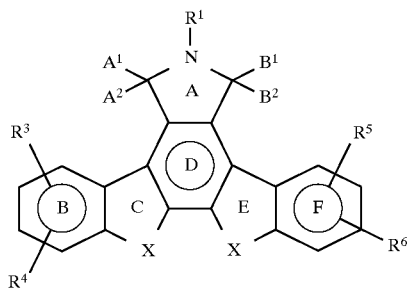

Preferably, $A^1$ and $A^2$ are selected pairwise from the group consisting of H, H; H, OH; and =O; and $B^1$ and $B^2$ are selected pairwise from the group consisting of H, H; H, OH; and =O; provided that $A^1$ and $A^2$, or $B^1$ and $B^2$, are =O.

Preferably, $R^1$ is H. When $R^1$ is $COR^9$ and $R^9$ is aryl, preferably $R^9$ is phenyl or naphthyl.

Preferably, X, at either position, or both positions, is an unsubstituted alkylene of 1–3 carbons, —O—, or —S—. When X has an $R^2$ substituent, a preferred $R^2$ group is $OR^{10}$. When the $R^2$ group is arylalkyl of 7–14 carbons, preferably it is benzyl. When $R^2$ is an alkyl, alkenyl, or alkynyl, preferably it is an alkyl, alkenyl, or alkynyl of 1–4 carbons. When $R^2$ is a substituted alkyl, alkenyl, or alkynyl, and the substituent is aryl, preferably the aryl is phenyl or naphthyl. When a substituent on $R^2$ is —$S(O)_yR^{11}$, and $R^{11}$ is aryl, preferably $R^{11}$ is phenyl or naphthyl. When a substituent on $R^2$ is —CH=$NNR^{11}R^{12}$ or —$SO_2NR^{12}R^{13}$, and $R^{12}$ or $R^{13}$ is aryl, preferably it is phenyl or naphthyl. When $R^{12}$ and $R^{13}$ together represent a linking group, preferably the linking group is —$(CH_2)_2$—$X^1$—$(CH_2)_2$—, where $X^1$ is selected from the group consisting of —O—; —S—; and —$CH_2$—.

Preferably, $R^3$, $R^4$, $R^5$, and $R^6$ are H. When at least one of $R^3$, $R^4$, $R^5$, and $R^6$ is aryl, preferably it is aryl of 6–10 carbons, and more preferably it is phenyl or naphthyl, provided that either $R^3$ or $R^4$ is H, and either $R^5$ or $R^6$ is H. When at least one of $R^3$, $R^4$, $R^5$, and $R^6$ is alkyl, alkenyl, or alkynyl of 1–8 carbons, preferably it is alkyl, alkenyl, or alkynyl of 1–4 carbons, provided that either $R^3$ or $R^4$ is H, and either $R^5$ or $R^6$ is H.

Wherever numerical ranges are specified herein, the range is inclusive. For example, "1–4 carbons" includes the values 1, 2, 3, and 4. Unless otherwise specified, wherever the terms "aryl" or "heteroaryl" are used herein, it is to be understood that the aryl or heteroaryl group can be substituted or unsubstituted.

As used in the definition of $R^{14}$, the term "amino acid" denotes a molecule containing both an amino group and a carboxyl group. It includes an "α-amino acid" which has its usual meaning as a carboxylic acid which bears an amino functionality on the carbon adjacent to the carboxyl group. α-Amino acids can be naturally occurring or non-naturally occurring. Amino acids also include "dipeptides" which are defined herein as two amino acids which are joined in a peptide linkage. Thus, constituents of dipeptides are not limited to α-amino acids, and can be any molecule containing both an amino group and a carboxyl group. Preferred are α-amino acids, dipeptides such as lysyl-β-alanine, and aminoalkanoic acids of 2–8 carbons, e.g., 3-dimethylaminobutyric acid.

Pharmaceutically acceptable salts of the fused isoindolone derivatives also fall within the scope of the compounds as disclosed herein. The term "pharmaceutically acceptable salts" as used herein means an inorganic acid addition salt such as hydrochloride, sulfate, and phosphate, or an organic acid addition salt such as acetate, maleate, fumarate, tartrate, and citrate. Examples of pharmaceutically acceptable metal salts are alkali metal salts such as sodium salt and potassium salt, alkaline earth metal salts such as magnesium salt and calcium salt, aluminum salt, and zinc salt. Examples of pharmaceutically acceptable ammonium salts are ammonium salt and tetramethylammonium salt. Examples of pharmaceutically acceptable organic amine addition salts are salts with morpholine and piperidine. Examples of pharmaceutically acceptable amino acid addition salts are salts with lysine, glycine, and phenylalanine.

Compounds provided herein can be formulated into pharmaceutical compositions by admixture with pharmaceutically acceptable nontoxic excipients and carriers. As noted above, such compositions may be prepared for use in parenteral administration, particularly in the form of liquid solutions or suspensions; or oral administration, particularly in the form of tablets or capsules; or intranasally, particularly in the form of powders, nasal drops, or aerosols; or dermally, via, for example, trans-dermal patches.

The composition may conveniently be administered in unit dosage form and may be prepared by any of the methods well known in the pharmaceutical art, for example, as described in *Remington's Pharmaceutical Sciences* (Mack Pub. Co., Easton, Pa., 1980). Formulations for parenteral administration may contain as common excipients sterile water or saline, polyalkylene glycols such as polyethylene glycol, oils and vegetable origin, hydrogenated naphthalenes and the like. In particular, biocompatible, biodegradable lactide polymer, lactide/glycolide copolymer, or polyoxyethylene-polyoxypropylene copolymers may be useful excipients to control the release of the active compounds. Other potentially useful parenteral delivery systems for these active compounds include ethylene-vinyl acetate copolymer particles, osmotic pumps, implantable infusion systems, and liposomes. Formulations for inhalation administration contain as excipients, for example, lactose, or may be aqueous solutions containing, for example, polyoxyethylene-9-lauryl ether, glycocholate and deoxycholate, or oily solutions for administration in the form of nasal drops, or as a gel to be applied intranasally. Formulations for parenteral administration may also include glycocholate for buccal administration, a salicylate for rectal administration, or citric acid for vaginal administration. Formulations for trans-dermal patches are preferably lipophilic emulsions.

The materials of this invention can be employed as the sole active agent in a pharmaceutical or can be used in combination with other active ingredients, e.g., other growth factors which facilitate neuronal survival or axonal regeneration in diseases or disorders, therapy for cancer or therapy for HIV infection.

The concentrations of the compounds described herein in a therapeutic composition will vary depending upon a number of factors, including the dosage of the drug to be administered, the chemical characteristics (e.g., hydrophobicity) of the compounds employed, and the route of administration. In general terms, the compounds of this invention may be provided in an aqueous physiological buffer solution containing about 0.1 to 10% w/v compound for parenteral administration. Typical dose ranges are from about 1 µg/kg to about 1 g/kg of body weight per day; a preferred dose range is from about 0.01 mg/kg to 100 mg/kg of body weight per day. The preferred dosage of drug to be administered is likely to depend on such variables as the type and extent of progression of the disease or disorder, the overall health status of the particular patient, the relative biological efficacy of the compound selected, and formulation of the compound excipient, and its route of administration.

III. Fused Isoindlolone Utilities

The fused isoindolones have evidenced important functional pharmacological activities which find utility in a variety of settings, including both research and therapeutic arenas. Generally, the activities of the fused isoindolones show positive effects on the function and/or survival of trophic factor responsive cells and demonstrate inhibition of enzymatic activity, namely trk and PKC.

Effect on the function and/or survival of trophic factor responsive cells, e.g., cells of a neuronal lineage, can be established using any of the following assays: (1) cultured spinal cord choline acetyltransferase ("ChAT") assay; or (2) cultured basal forebrain neuron ("BFN") ChAT activity assay. Inhibition of enzymatic activity can be determined using PKC inhibition assays and trk tyrosine kinase inhibition assays.

As used herein, the term "effect" when used to modify the terms "function" and "survival" means a positive or negative alteration or change. An effect which is positive can be referred to herein as an "enhancement" or "enhancing" and an effect which is negative can be referred to herein as "inhibition" or "inhibiting."

As used herein, the terms "enhance" or "enhancing" when used to modify the terms "function" or "survival" means that the presence of a fused isoindolone has a positive effect on the function and/or survival of a trophic factor responsive cell compared with a cell in the absence of the fused isoindolone. For example, and not by way of limitation, with respect to the survival of, e.g., a cholinergic neuron, the fused isoindolone would evidence enhancement of survival of a cholinergic neuronal population at risk of dying (due to, e.g., injury, a disease condition, a degenerative condition or natural progression) when compared to a cholinergic neuronal population not presented with such fused isoindolone, if the treated population has a comparatively greater period of functionality than the non-treated population.

As used herein, "inhibit" and "inhibition" mean that a specified response of a designated material (e.g., enzymatic activity) is comparatively decreased in the presence of a fused isoindolone.

As used herein the term "neuron," "cell of neuronal lineage" and "neuronal cell" includes, but is not limited to, a heterogeneous population of neuronal types having singular or multiple transmitters and/or singular or multiple functions; preferably, these are cholinergic and sensory neurons. As used herein, the phrase "cholinergic neuron" means neurons of the Central Nervous System (CNS) and Peripheral Nervous System (PNS) whose neurotransmitter is acetylcholine; exemplary are basal forebrain and spinal cord neurons. As used herein, the phrase "sensory neuron" includes neurons responsive to environmental cues (e.g., temperature, movement) from, e.g., skin, muscle and joints; exemplary is a neuron from the DRG.

A "trophic factor-responsive cell," as defined herein, is a cell which includes a receptor to which a trophic factor can specifically bind; examples include neurons (e.g., cholinergic and sensory neurons) and non-neuronal cells (e.g., monocytes and neoplastic cells).

As used herein, the term "trk" refers to the family of high affinity neurotrophin receptors presently comprising trk A, trk B and trk C, and other membrane associated proteins to which a neurotrophin can bind.

A. Effect on the function and/or survival of trophic factor responsive cells

The disclosed fused isoindolones can be used to enhance the function and/or survival of cells of neuronal lineage. In this context, the fused isoindolones can be utilized individually or with other fused isoindolones, or in combination with other beneficial molecules such as indolocarbozoles which also evidence the ability to effect the function and/or survival of a designated cell.

A variety of neurological disorders are characterized by neuronal cells which are dying, injured, functionally comprised, undergoing axonal degeneration, at risk of dying, etc. These disorders include, but are not limited to: Alzheimer's; motor neuron disorders (e.g. amyotrophic lateral sclerosis); Parkinson's; cerebrovascular disorders (e.g., stroke, ischaemia); Huntington's; AIDS dementia; epilepsy; multiple sclerosis; peripheral neuropathies (e.g., those affecting DRG neurons in chemotherapy-associated peripheral neuropathy) including diabetic neuropathy; disorders induced by excitatory amino acids; disorders associated with concussive or penetrating injuries of the brain or spinal cord.

As set forth in the Examples of this section of the disclosure, the ability of a fused isoindolone to enhance the function and/or survival of cells of a neuronal lineage can be determined by employing (1) spinal cord ChAT activity assay; or (2) basal forebrain ChAT activity assay.

ChAT catalyzes the synthesis of the neurotransmitter acetylcholine and is considered an enzymatic marker for a functional cholinergic neuron. A functional neuron is also capable of survival. Neuron survival is assayed by quantitation of the specific uptake and enzymatic conversion of a dye (e.g., calcein AM) by living neurons.

Because of their varied utilities, the fused isoindolones disclosed herein find utility in a variety of settings. The compounds can be used in the development of in vitro models of neuronal cell survival, function, identification, or for the screening of other synthetic compounds which have activities similar to that of the fused isoindolones. The compounds can be utilized in a research environment to investigate, define and determine molecular targets associated with functional responses. For example, by radiolabelling a fused isoindolones associated with a specific cellular function (e.g., mitogenesis), the target entity to which the fused isoindolones binds can be identified, isolated, and purified for characterization.

Degeneration, death or non-functioning of neurons is a feature of many human neurological disorders, including, but not limited to, Alzheimer's; motor neuron disorders (e.g., ALS); Parkinson's; cerebrovascular disorders (e.g., stroke, ischaemia); Huntington's; AIDS dementia; epilepsy; multiple sclerosis; concussive or penetrating injuries of the brain or spinal cord; peripheral neuropathies; and disorders induced by excitatory amino acids. Because the disclosed compounds have evidenced utility in, e.g., enhancement of ChAT activity, the utility of the compounds in the treatment of disorders associated with, e.g., decreased ChAT activity or the death of DRG neurons, is within the scope of this invention.

Example III(A)(1): Spinal Cord ChAT Activity Assay

As noted, ChAT is a specific biochemical marker for functional cholinergic neurons. Cholinergic neurons represent the major cholinergic input into the hippocampal formation, olfactory nucleus, interpeduncular nucleus, cortex, amygdala, and parts of the thalamus. In the spinal cord, the motor neurons are cholinergic neurons which contain ChAT (Phelps et al., *J. Comp. Neurol.* 273: 459–472 (1988)). ChAT activity has been used to study the effects of neurotrophins (e.g., NGF or NT-3) on the survival and/or function of cholinergic neurons. The ChAT assay also serves as an indication of the regulation of ChAT levels within cholinergic neurons.

Fused isoindolone derivatives increased ChAT activity in the dissociated rat embryonic spinal cord culture assay (FIG. 1). Compound I-2 increased ChAT activity 150% over control cultures (not treated with the fused isoindolone) after allowing a 2–3 hour plating period for cells to attach to control tissue culture wells. In these assays, a fused isoindolone was directly added to a dissociated spinal cord culture. Compounds of the invention increased spinal cord ChAT activity. Compounds which increased ChAT activity at least 120% of the control activity are considered active. Increased ChAT activity was observed after a single application of the fused isoindolone. The compound was added on the same day the dissociated spinal cord cell culture was initiated. Increased ChAT activity was detectable 48 hours later.

Methods: Fetal rat spinal cord cells were dissociated, and experiments were performed as described (Smith et al., *J. Cell Biology* 101: 1608–1621 (1985); Glicksman et al., *J. Neurochem.* 61: 210–221 (1993)). Dissociated cells were prepared from spinal cords dissected from rats (embryonic day 14–15) by standard trypsin dissociation techniques (Smith et al., *J. Cell Biology* 10: 1608–1621 (1985)). Cells were plated at $6 \times 10^5$ cells/cm² on poly-l-ornithine coated plastic tissue culture wells in serum-free N2 medium supplemented with 0.05% bovine serum albumin (BSA) (Bottenstein et al., *PNAS USA* 76: 514–517 (1979)). Cultures were incubated at 37° C. in a humidified atmosphere of 5% $CO_2$/95% air for 48 hours. ChAT activity was measured after 2 days in vitro using a modification of the Fonnum procedure (Fonnum, *J. Neurochem.* 24: 407–409 (1975)) according to McManaman et al. and Glicksman et al. (McManaman et al., *Developmental Biology* 125: 311–320 (1988); Glicksman et al., *J. Neurochem.* 61: 210–221 (1993)).

Example III(A)(2): Basal Forebrain ChAT Activity Assay

Figure 2:
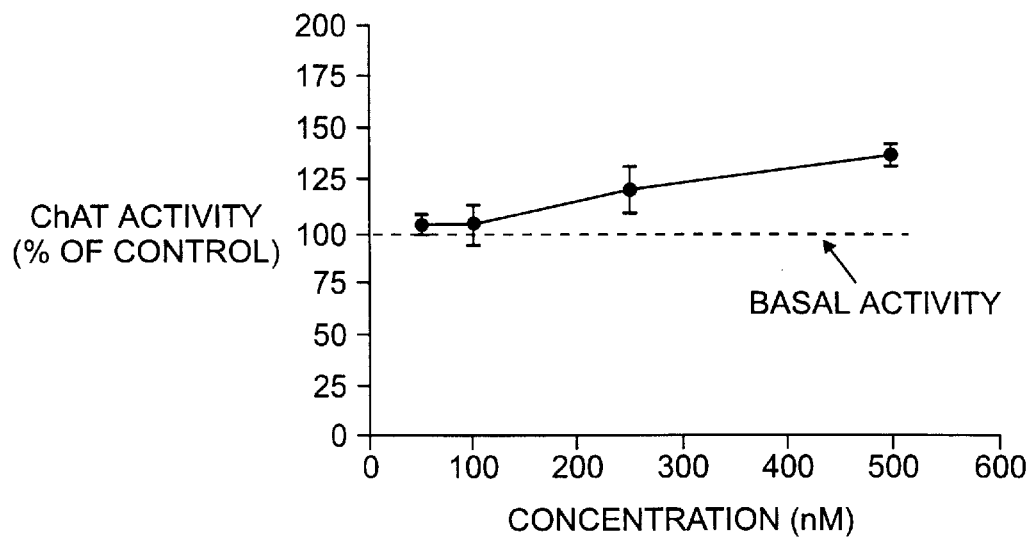
FIG. 2 is a graph evidencing that fused isoindolones promote ChAT activity in basal forebrain.

Fused isoindolone derivatives were tested for the ability to increase ChAT activity of basal forebrain cultures. Fused isoindolones were found to increase ChAT activity in basal forebrain cultures (FIG. 2). Control cultures did not receive a fused isoindolone.

In preliminary assays of basal forebrain ChAT activity, compounds I-3 and I-4 did not increase ChAT activity.

Methods: The basal forebrain was dissected from rat embryos (day 17 or 18 embryos) and the cells were dissociated with a neutral protease (Dispase™, Collaborative Research). Neurons were plated at a density of $5 \times 10^4$ cells/well ($1.5 \times 10^5$ cells/cm²) in poly-l-ornithine and laminin coated plates. Cells were cultured in serum-free N2 medium containing 0.05% BSA at 37° C. in a humidified atmosphere, 5% $CO_2$/95% air. ChAT activity was assessed 5 days after plating by using the ChAT assay as described in Example III(A)(1).

B. Inhibition of Enzymatic Activity

The ability of the indolocarbazole K-252a, for example, to inhibit the enzymatic activity of PKC is well known and documented. Inhibition of PKC activity has been suggested as an approach for inhibiting, mediating, reducing and/or preventing a variety of disease states, including inflammatory diseases, allergy and cancerous conditions, as indicated in the following representative references: U.S. Pat. Nos. 4,877,776, and 4,923,986; published European Patent Specification 558,962 (published Sep. 8, 1993 in the name of E. R. Squibb & Sons, Inc.); Tadka, T. et al., 170(3) *Biochem. Biophys. Res. Comm.* 1151, 1980). The tyrosine kinases, of which trk is a member, are enzymes which catalyze the transfer of the γ-phosphate of ATP to the hydroxyl group of tyrosine on many key proteins. Activated protein tyrosine kinases have been identified as the products of approximately half of known oncogenes (see Chang, C-J & Geahlen, R. L. 55(11) *J. Nat. Prods.* 1529, 1992). Inhibiting, mediating, reducing and/or preventing a variety of cancerous conditions via inhibition of protein kinases has been set forth (see Chang, C-J, supra).

Because of the important association between protein kinase activity and certain diseases and disorders (e.g. cancer), fused isoindolones also find utility in both research and therapeutic settings. For example, in a research environment, the compounds can be used in the development of assays and models for further enhancement of the understanding of the roles that inhibition of protein kinase (e.g., PKC, trk tyrosine kinase) play in the mechanistic aspects of the associated disorders and diseases. In a therapeutic setting, the compounds which inhibit these enzymatic activities can be used to inhibit the deleterious consequences of these enzymes with respect to disorders such as cancer.

The data demonstrate inhibition of enzymatic activity using the disclosed fused isoindolones as determined by the following assays: (1) PKC activity inhibition assay; (2) trkA tyrosine kinase activity inhibition assay.

Example III(B)(1): PKC Activity Inhibition Assay

Fused isoindolones inhibited the activity of protein kinase C (Table VI). The protein kinase C assay has been disclosed (Murakata et al., U.S. Pat. No. 4,923,986; Kikkawa et al., *J. Biol. Chem.* 257: 13341–13348 (1982)). The assay was performed with several concentrations of fused isoindolones. The concentration at which protein kinase C was 50% inhibited ($IC_{50}$) was determined.

TABLE I

| Protein Kinase C Inhibition | |
|---|---|
| COMPOUND | PKC INHIBITION $IC_{50}$ (μM) |
| I-1 | 0.65 |
| I-2 | 2.00 |

Example III(B)(2): trkA Tyrosine Kinase Activity Inhibition Assay

Fused isoindolones inhibited trkA tyrosine kinase activity as determined by ELISA. trkA is a high affinity receptor for neurotrophins. Fused isoindolones were added to 96-well microtiter plates that were previously coated with a phosphorylation substrate (phospholipase C-γ (PLCγ)/pGEX fusion protein) (see Rotin, et al., 11 EMBO J. 559, 1992). These compounds were then tested for the ability to inhibit substrate phosphorylation by the trkA tyrosine kinase.

TABLE II

Inhibition of trkA Tyrosine Kinase Activity

| COMPOUND | trk A INHIBITION IC$_{50}$ ($\mu$M) |
|---|---|
| I-1 | NT |
| I-2 | 0.19 |

Methods: 96-well ELISA plates (Nunc) were coated with 100 μl/well of the phosphorylation substrate (40 μg/ml) PLCγ/pGEX fusion protein) in 20 mM Tris, pH 7.6, 137 mM NaCl, and 0.02% NaN$_3$ overnight at 4° C. Plates were then washed three times with TBST (20 mM Tris, pH 7.6, 137 mM NaCl, 0.2% Tween-20) and subsequently blocked with 3% bovine serum albumin (BSA) in TBST for 1 hour at 37° C. Plates were washed three times with TBST, followed by two washes with TBS (TBST sans Tween-20). Fused pyrrolocarbozoles were then added at various concentrations to a reaction mixture (50 mM HEPES, pH 7.4, 5 mM MnCl$_2$, 5 mM MgCl$_2$, 140 mM NaCl, 16 μM ATP, and 15 ng trkA in a total volume of 100 μL). As a negative control, 100 mM EDTA was included in the reaction solution. The plates were then incubated at 37° C. for 15 min. The detection antibody, monoclonal anti-phosphotyrosine antibody (UBI), was added at a dilution of 1:2000 in TBST, and incubated for 1 hour at 37° C. Plates were then washed three times with TBST, followed by a 1 hour incubation at 37° C. with alkaline phosphatase-labeled goat anti-mouse IgG (1:2000 in TBST (Bio-Rad)). After washing three times with TBST followed by two washes with TBS, a colored product was produced by using NADPH as substrate for alkaline phosphatase, and the coupled reactions of diaphorase and alcohol dehydrogenase (GIBCO-BRL ELISA amplification system). The colored product was read at 490 nm in a microplate reader (Biotek).

IV. General Description of Synthetic Processes

Figure 3:
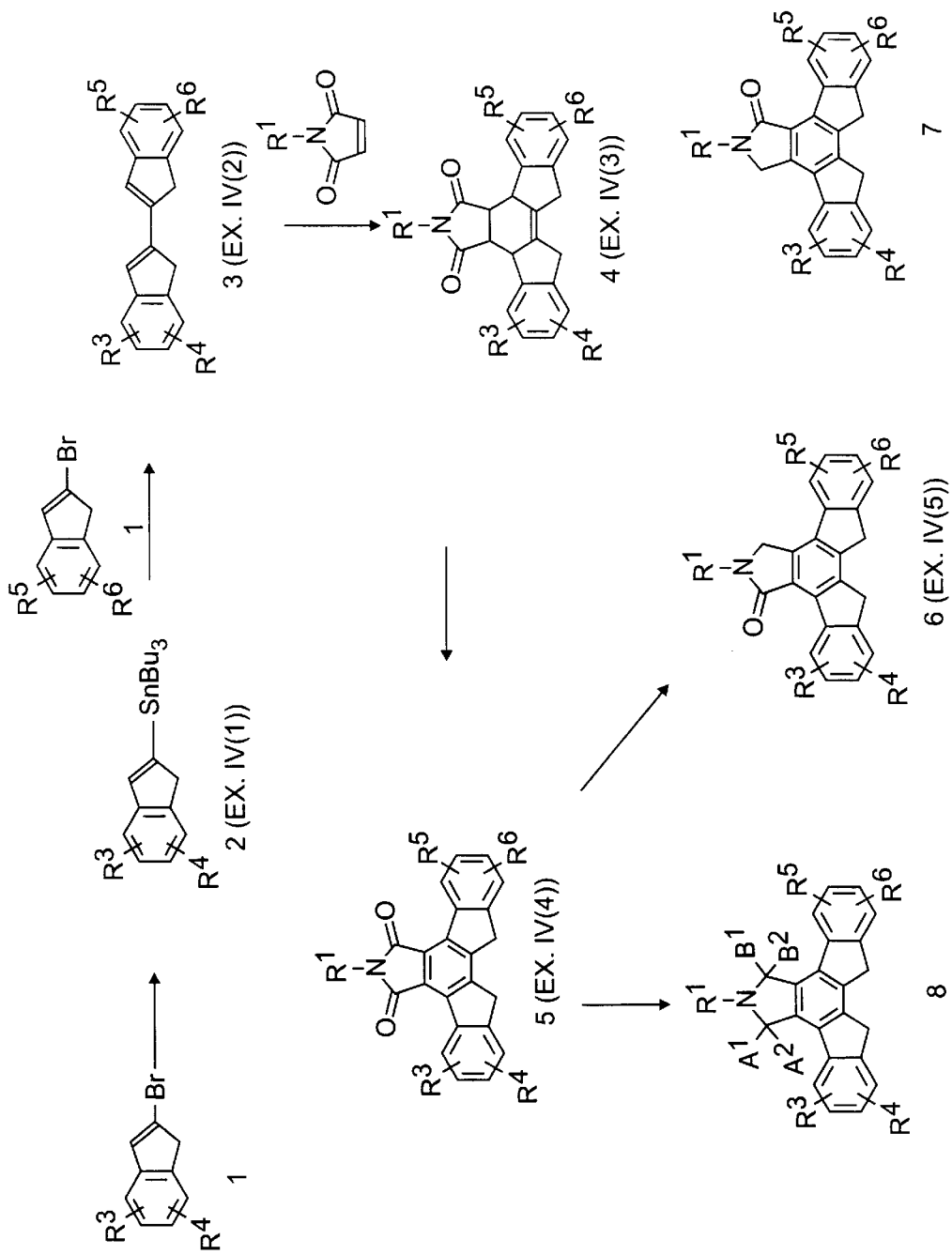
FIG. 3 shows a scheme for the synthesis of bis-indene derivatives.

Compounds of the invention are prepared by the general processes described below. Compounds in which X=CH$_2$, CH$_2$, are outlined in FIG. 3. The known 2-2' biindene (3, R$^1$, R$^2$, R$^3$, R$^4$, R$^5$, R$^6$,=H; Example IV(2)) was prepared by an improved method by palladium catalyzed coupling of 2-(tributylstannyl)indene (2) with 2-bromoindene (1). 2-Bromoindene (1), prepared using a literature procedure (J. Org. Chem., 1982, 47, 705) was used to prepare 2-(tributylstannyl)indene (2) (Example IV(1)) (FIG. 3). Aryl substituted 2-bromoindenes may be prepared from indenes, or 1- or 2-indanones by those skilled in the art of organic synthesis.

Cycloaddition reaction of compounds of the general formula 3 with maleimide (method 1), preferably at temperatures of 160°–200° C., forms the corresponding tetrahydroisoindolyl-dione 4 (R$^1$, R$^2$, R$^3$, R$^4$, R$^5$, R$^6$,=H; Example IV(3)). Cycloaddition reactions of 2-(2-indenyl) indenes have not been described previously. Cycloaddition reactions of dienes with maleimides are well known (see for example J. Chem. Soc., Perkin Trans. 1, 1990, 2475). Example IV(3) is dehydrogenated according to conventional processes with, for example, 2,3-dichloro-5,6-dicyano-1,4-benzoquinone, Pd on active charcoal, sulfur or sodium nitrite (U.S. Pat. No. 4,912,107 and references cited therein) to give the corresponding aromatized isoindolone-imide derivative 5 (Example IV (4))(Compound I-1, R$^1$, R$^2$, R$^3$, R$^4$, R$^5$, R$^6$,=H). Lactams of general formula 6 (Example IV(5), Compound I-2, R$^1$, R$^2$, R$^3$, R$^4$, R$^5$, R$^6$,=H;) can be prepared by the reduction of imide 5 with reducing agents (e.g., zinc amalgam, gaseous hydrogen chloride, zinc amalgam in acetic acid, zinc in glacial acetic acid, or hydride reducing agents such as lithium aluminum hydride). In cases where R$^2$, R$^3$, R$^4$, R$^5$, or R$^6$ are other than H, lactam regioisomers (general formulas 6 and 7) are formed. The lactam regioisomers can be separated by standard processes such as recrystallization or chromatography, for example, column chromatography or HPLC. The imides may be reduced to hydroxylactams (8, FIG. 3) where A$^1$, A$^2$ or B$^1$, B$^2$=H,OH by hydride reducing agents such as borohydrides or aluminum hydrides (U.S. Pat. Nos. 4,192,107 and 4,923,986 and references therein). The resulting hydroxyl group is easily converted to alkoxy or thioalkyl groups (U.S. Pat. No. 4,923,986). Derivatives in which A$^1$, A$^2$ or B$^1$, B$^2$ together represent S or N are prepared as described in European Patent Application No. 0 508 792 AI.

In Method II (FIG. 15), cycloaddition reaction of the appropriate diene with acetylene dicarboxylates (R=lower alkyl) gives the corresponding aromatic compounds of general formula 39. The isobenzofurans (general formula 40) may be obtained by dealkylation of the ester with nucleophiles (e.g., LiI, NaCN, NaSCH$_3$, NaSCN, etc.) followed by anhydride formation using acetic anhydride. Imides of general formula 41 may be prepared by the reaction of isobenzofurans of formula 40 with 1,1,1,3,3,3-hexamethyldisilazane and methanol (Tetrahedron Lett. 1990, 31, 5201–5204). Lactams of general formula 42 can be prepared by the reduction of imide 41 with reducing agents (e.g., zinc amalgam, gaseous hydrogen chloride, zinc amalgam in acetic acid, zinc in glacial acetic acid, or hydride reducing agents such as lithium aluminum hydride). In cases where R$^2$, R$^3$, R$^4$, R$^5$, or R$^6$ are other than H, or the X groups are not the same, lactam regioisomers are formed (general structures 42 and 43). The lactam regioisomers may be separated by standard processes such as recrystallization or chromatography, for example, column chromatography or HPLC. The imides may be reduced to hydroxylactams (44, FIG. 15) as described previously.

Figure 13:
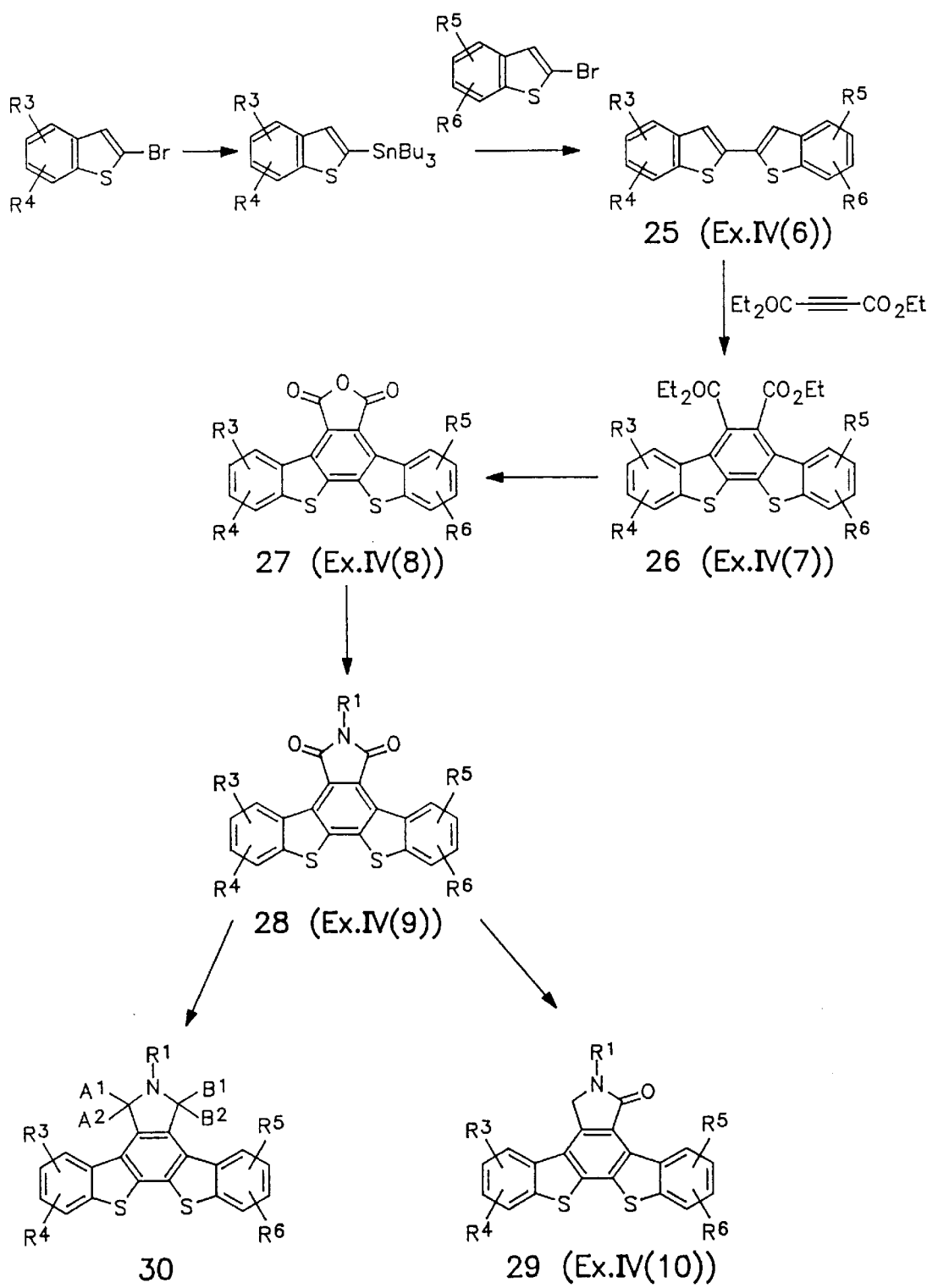
FIG. 13 shows a scheme for the synthesis of bis-benzothiaphene derivatives.

Specifically, compounds in which X=S are outlined in FIG. 13. 2,2'-Bi-benzothiaphene (25, R$^1$, R$^2$, R$^3$, R$^4$, R$^5$, R$^6$,=H; Example IV(6)) was prepared by the same method as that described for compound 3. Cycloaddition reaction of compounds of general formula 25 with diethyl acetylenedicarboxylate, preferably at temperatures of 180°–200° C., forms the corresponding carboethoxydibenzothiaphene (26, R$^1$, R$^2$, R$^3$, R$^4$, R$^5$, R$^6$,=H; Example IV(7)). Cycloadditions of 2,2'-bisbenzothiaphenes have not been described previously. The carboethoxydibenzothiaphenes may be converted to the corresponding isobenzofurans (27, R$^1$, R$^2$, R$^3$, R$^4$, R$^5$, R$^6$,=H; Example IV(8)) by dealkylation of the ester with nucleophiles (e.g., LiI, NaCN, NaSCH$_3$, NaSCN, etc.) followed by anhydride formation in acetic anhydride (Method II). Imides of general formula 28 ((Compound I-3), R$^1$, R$^2$, R$^3$, R$^4$, R$^5$, R$^6$,=H; Example IV(9)) may be prepared by the reaction of isobenzofuran 27 with 1,1,1,3,3,3-hexamethyldisilazane and methanol, as described above (Method II). Lactams of general formula 29 ((Compound I-4), R$^1$, R$^2$, R$^3$, R$^4$, R$^5$, R$^6$,=H; Example IV(10)) may be prepared by the reduction of imide 28 with reducing agents as described in Method I. The imides may be reduced to hydroxylactams (30, FIG. 13) as described previously.

Figure 14:
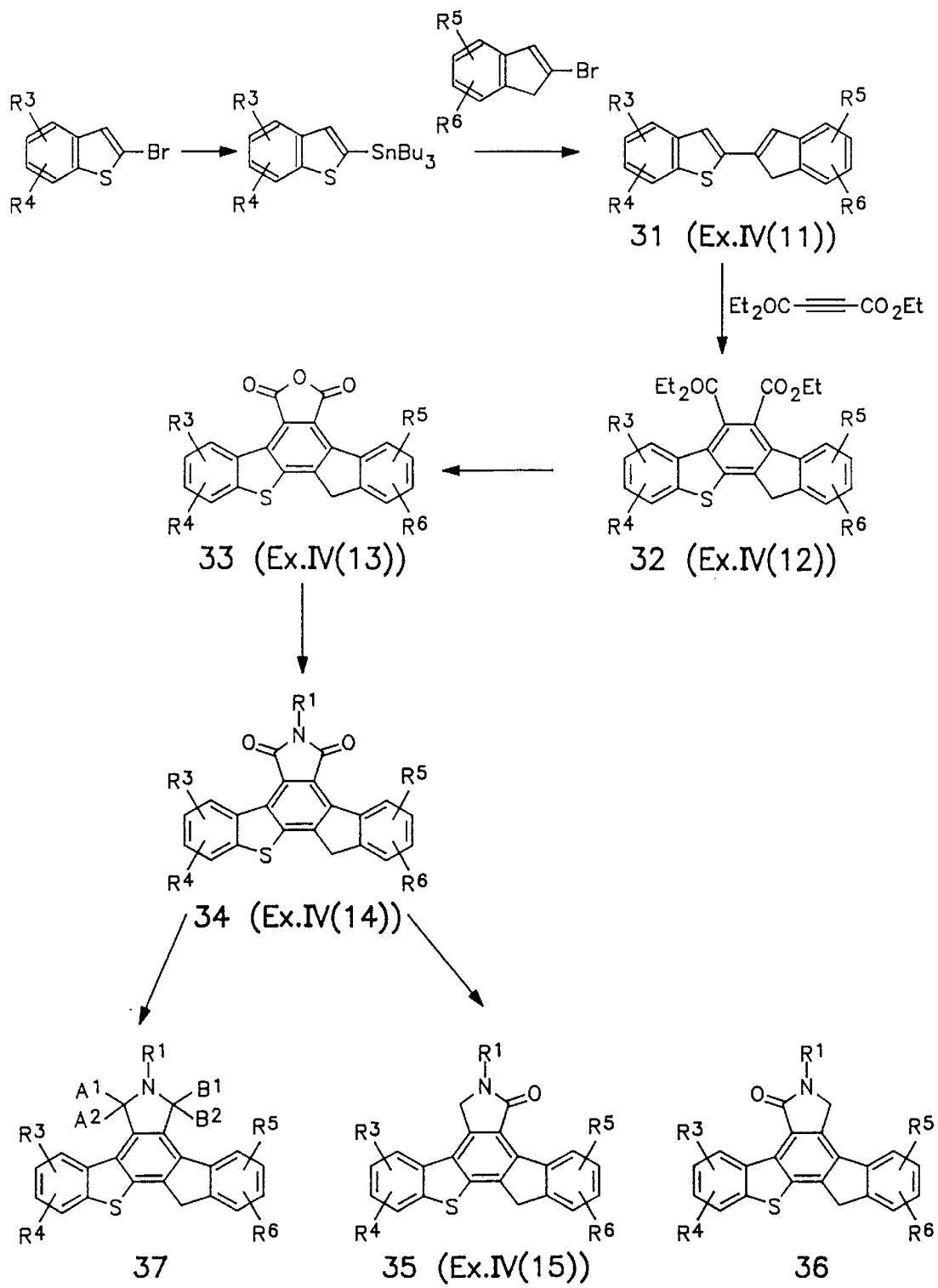
FIG. 14 shows a scheme for the synthesis of indenyl-benzothiaphene derivatives.

The synthesis of the unsymmetrical indenyl-benzothiaphene (X=S, CH$_2$) is outlined in FIG. 14. The 2-(2'-indenyl)benzothiaphene (31, R$^1$, R$^2$, R$^3$, R$^4$, R$^5$, R$^6$,=H; Example IV(11)) was prepared by the method previously described for 3. Cycloaddition reaction of compounds of the general formula 31 with diethylacetylene dicarboxylate, forms the corresponding carboethoxydibenzothiaphene (32, R$^1$, R$^2$, R$^3$, R$^4$, R$^5$, R$^6$,=H; Example IV(12)). The carboethoxydibenzothiaphenes 32 were converted to the corresponding isobenzofurans (33, R$^1$, R$^2$, R$^3$, R$^4$, R$^5$, R$^6$,=H; Example IV(13)) by dealkylation of the ester with nucleophiles followed by anhydride formation in acetic anhydride as described previously. Imides of general formula 34 ((Compound I-5), R$^1$, R$^2$, R$^3$, R$^4$, R$^5$, R$^6$,=H; Example IV(14)) may be prepared by the same methods in FIG. 13. Lactams of general formula 35 ((Compound I-6), R$^1$, R$^2$, R$^3$, R$^4$, R$^5$, R$^6$, =H; Example IV(10)) may be prepared by the reduction of imide 34 with reducing agents (e.g., zinc amalgam, gaseous hydrogen chloride, zinc amalgam in acetic acid, zinc in glacial acetic acid, or hydride reducing agents such as lithium aluminum hydride). In cases where R$^2$, R$^3$, R$^4$, R$^5$, or R$^6$ are other than H, lactam regioisomers are formed. The lactam regioisomers may be separated by standard processes such as recrystallization or chromatography, for example, column chromatography or HPLC. The imides may be reduced to hydroxylactams (37, FIG. 14) as described previously.

Figure 4:
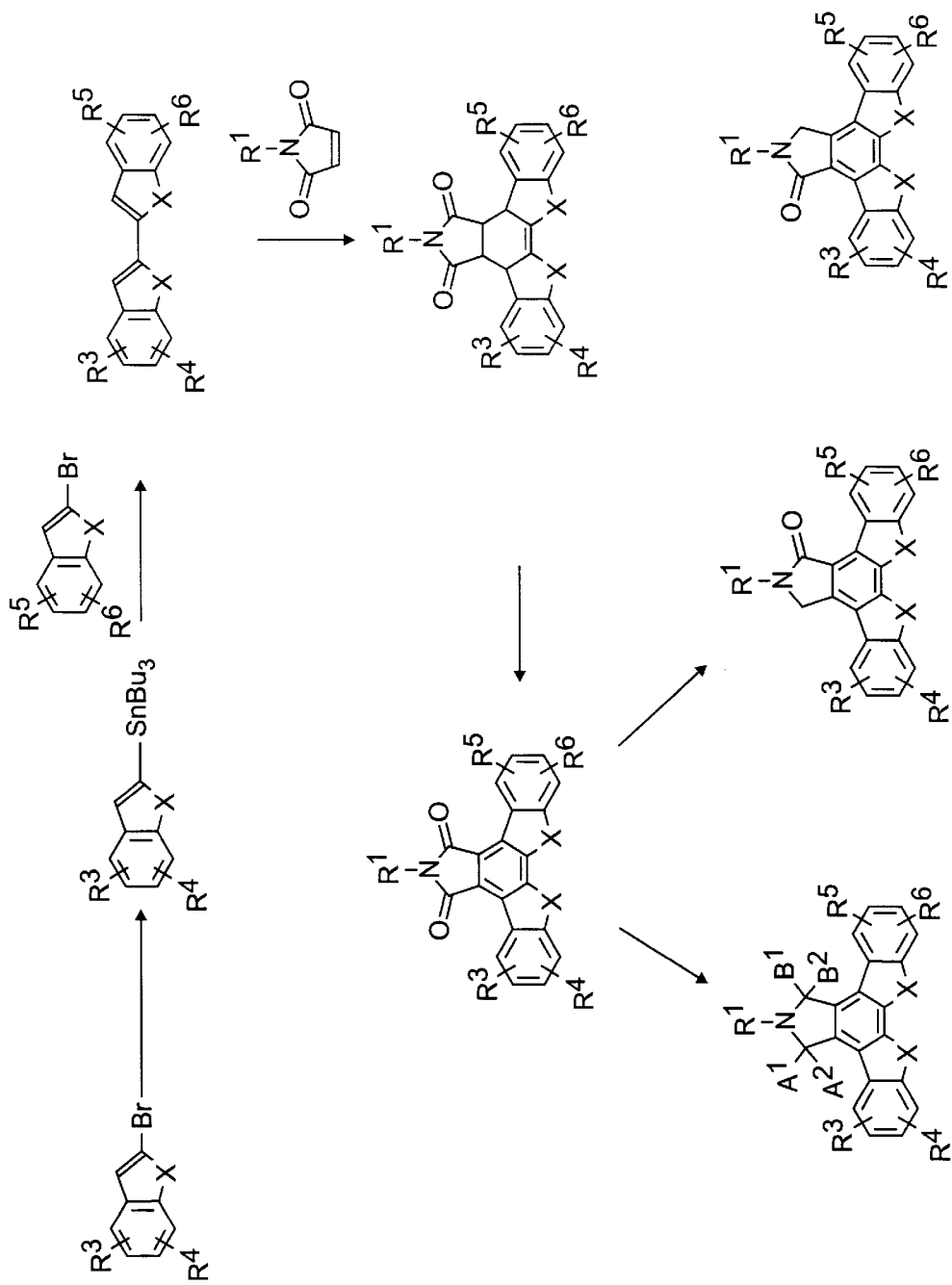
FIG. 4 shows a scheme for the synthesis of fused isoindolones.
Figure 5:
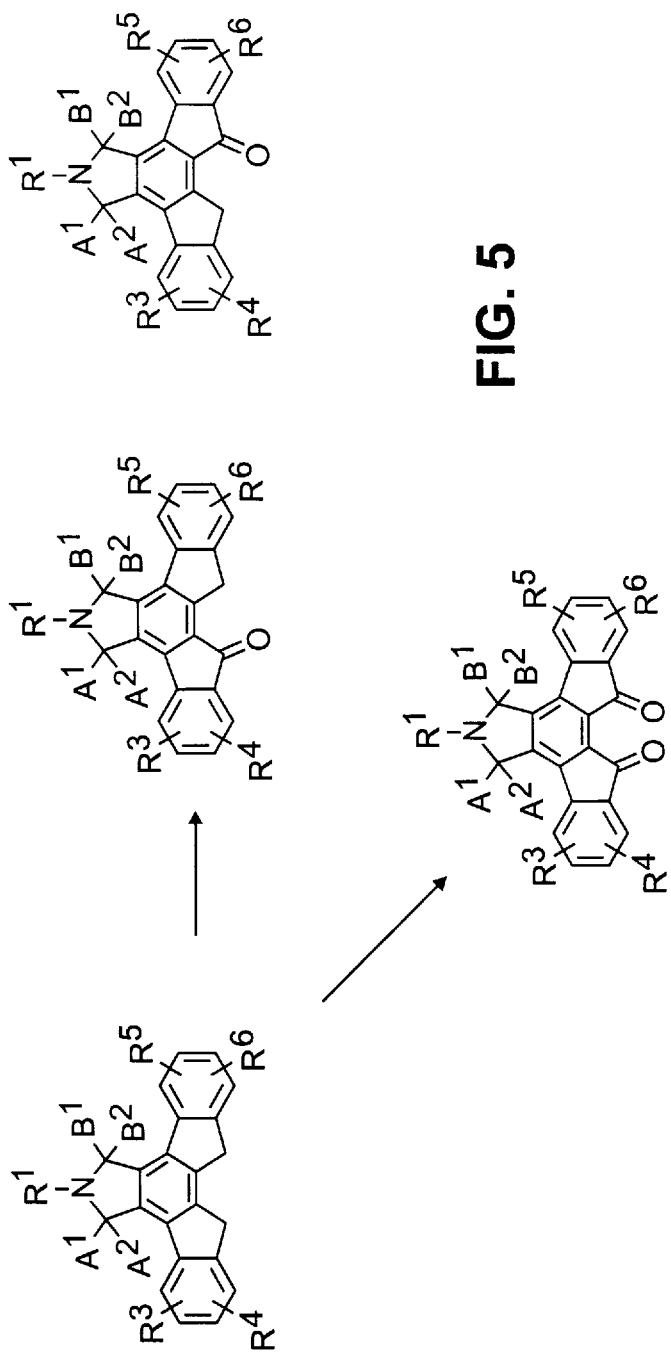
FIG. 5 shows a scheme for the synthesis of fused isoindolones in which X is —C(=O)—.
Figure 6:
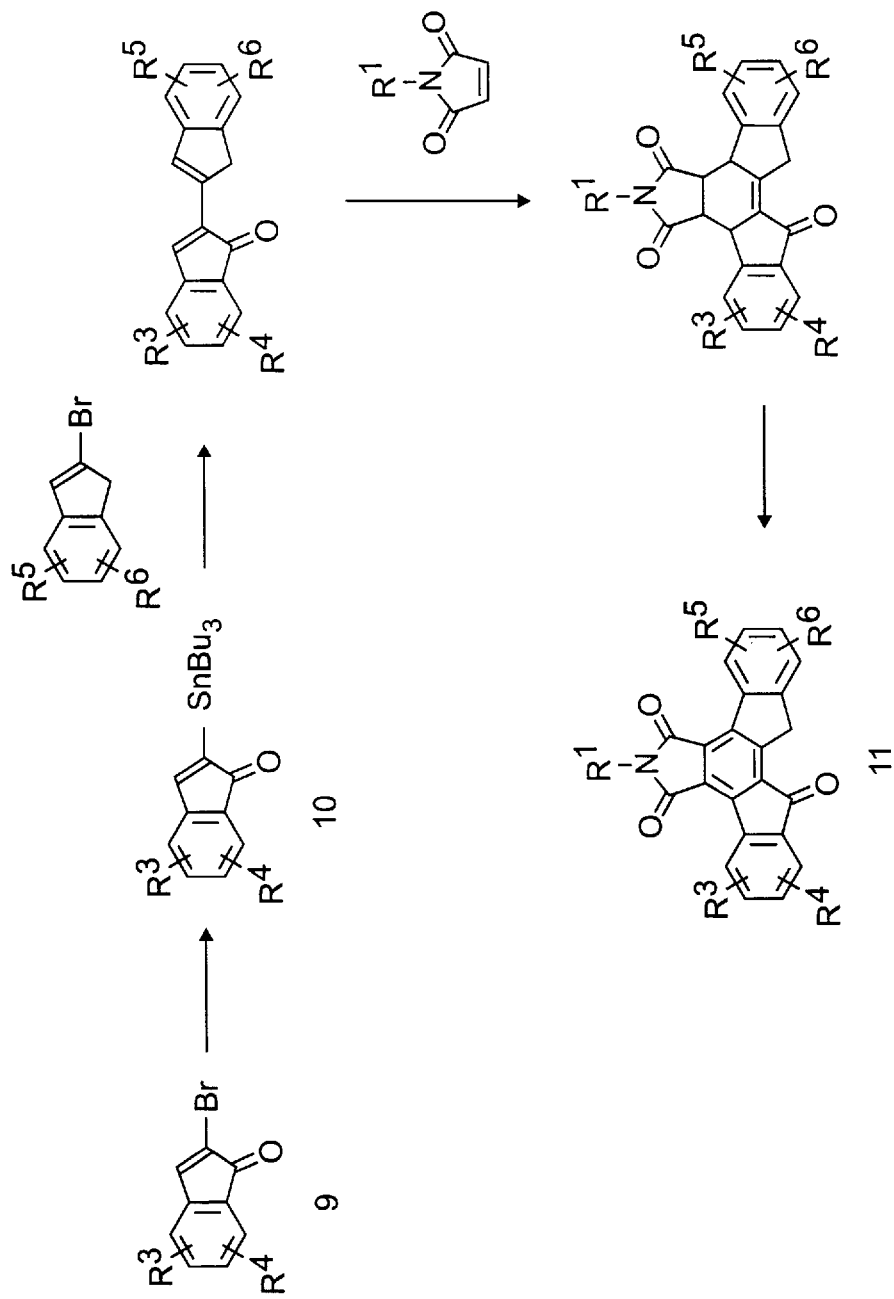
FIG. 6 shows a scheme for the synthesis of fused isoindolones (X=carbonyl) from 1-indanones.
Figure 7:
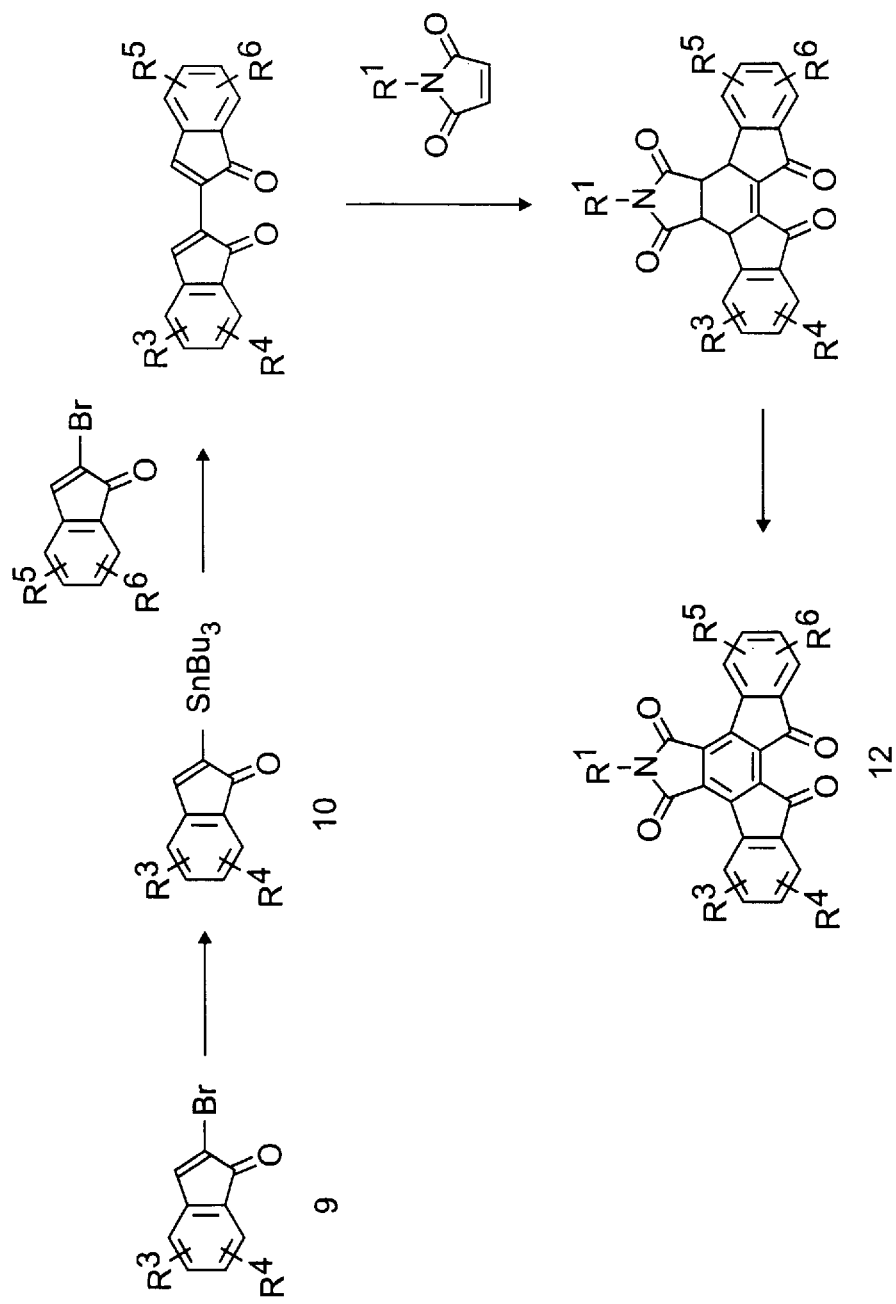
FIG. 7 shows a scheme for the synthesis of fused isoindolones which contain two carbonyl groups.

Fused isoindolone derivatives of general formula II in which X=CH$_2$CH$_2$, or CH=CH, are prepared by the procedures described for 6 or 7 (FIG. 3) except the 2-bromoindene and/or 2-(tributylstannyl)indene is replaced with a 2-bromo- or 2-(tributylstannyl)-3,4-dihydronaphthylene derivative (FIG. 4). Aryl substituted 2-bromo-3,4-dihydronaphthylenes may be prepared from 1- or 2-tetralones by those skilled in the art of organic synthesis. Replacement of the indene derivatives with a 2-benzocycloheptene derivative (J. Am. Chem. Soc. 13: 1344, (1991); J. Org. Chem. 44: 1342 (1979)) gives fused isoindolones of Formula II, where X=CH$_2$CH$_2$CH$_2$. Ketone derivatives where X is C=O may be prepared by oxidation of either the imide (5) or lactam (6 or 7) using standard oxidizing reagents (e.g., SeO$_2$, CrO$_3$, Na$_2$CrO$_7$, or MnO$_2$) (FIG. 5). Alternatively, X=(C=O, H) derivatives (11) may be prepared by starting with 2-bromoinden-1-one (9) (J. Org. Chem., 1994, 59, 3453) which may be used to prepare 2-(tributylstannyl)inden-1-one (10) by the method described in Example IV(1) (FIG. 6). Similarly X=(C=O, C=O) derivatives (12) may be prepared by reacting 2-bromoinden-1-one (9) with 2-(tributylstannyl)inden-1-one (FIG. 7).

Figure 8:
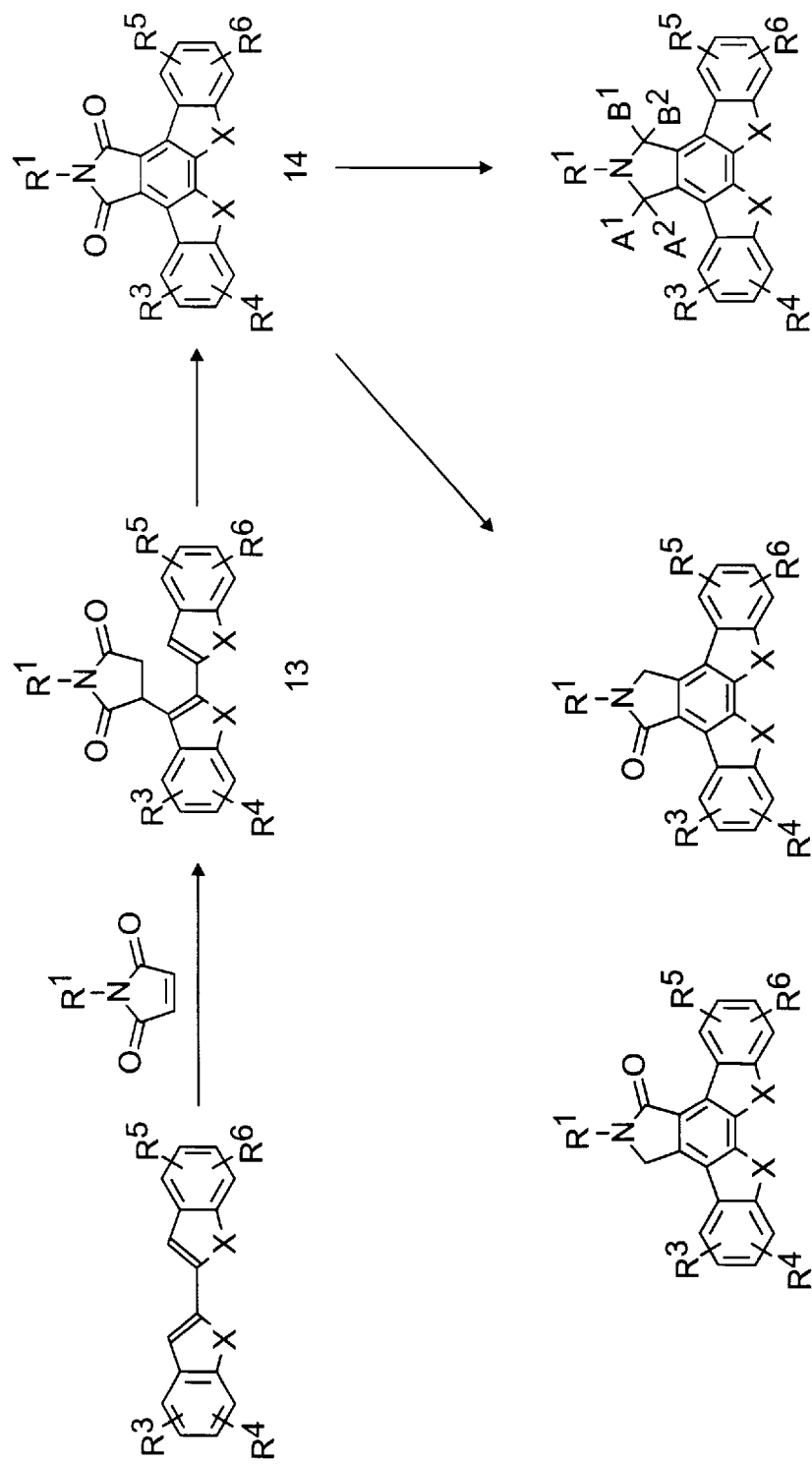
FIG. 8 shows a scheme for the synthesis of fused isoindolones using a Michael reaction.
Figure 15:
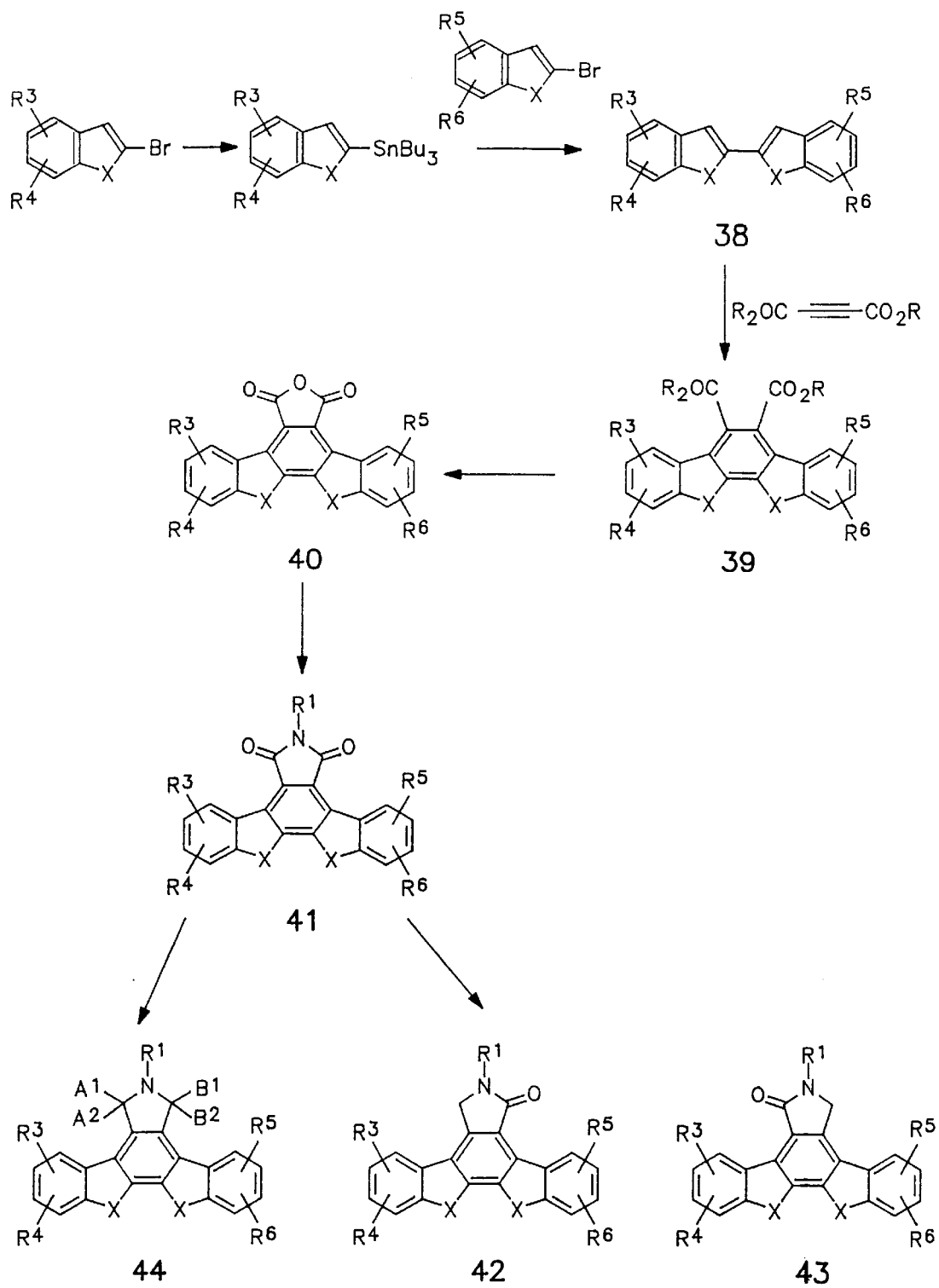
FIG. 15 shows a scheme for the synthesis of fused isoindolones using a Diels-Alder reaction with acetylene dicarboxylate.

Compounds with other X groups such as, X=S, O, or C=O (Formula II) can be prepared by cycloaddition reaction with the appropriate diene and maleimide as described in Method I (FIG. 4) or by processes described for Method II (FIG. 15). For example, the 2-(2-(1-oxoindenyl))indene (X=(C=O), CH$_2$), 2,2'-(1-oxo)biindene (X=(C=O), (C=O)), 2-(2-indenyl)benzothiophene (X=CH$_2$, S), 2-(2-indenyl)benzofuran (X=CH$_2$, O) 2,2'-bi-benzothiophen (X=S, S), 2-(2-benzothienyl)benzofuran (X=S, O) may each be prepared by coupling the corresponding 2-tributylstannyl derivative with the appropriate 2-bromo-aryl or -heteroaryl derivative. Preparation of the desired compounds may also be achieved by treatment of, for example, 2-(2-benzothienyl)benzofuran (X=S, O) or 2-(2-benzothienyl) benzothiophene (X=S, S) with maleimide in the presence of an acidic catalyst such as trifluoroacetic acid, or a Lewis acid (SnCl$_4$, Et$_2$AlCl) which gives a compound of general structure 13 (FIG. 8). These compounds can be cyclized to form the corresponding fused isoindolone derivatives 14, by treatment with a catalyst, for example, Pd(OAc)$_2$ in glacial acetic acid or Pd(OAc)$_2$, tetrachloro-1,4-benzoquinone in C$_2$H$_4$Cl$_2$ (FIG. 8).

The palladium-catalyzed cross-coupling methodology, known to those skilled in the art of organic synthesis, is used to prepare other derivatives, for example, where X in FIG. 8 is 1–3 carbons (inclusive), by coupling the vinyl-2-(trifluoromethanesulfonate) derivative of the corresponding cyclic ketone, or a 2-triflate derivative of the appropriate aryl or heteroaryl moiety with an appropriate tin derivative previously described.

Derivatives in which the nitrogen containing R$^1$ is bound by hydrogen can be converted to an R$^1$ group as described for Formula I (U.S. Pat. No. 4,923,986).

Derivatives of Formula I in which R$^3$, R$^4$, R$^5$, or R$^6$ substituents are other than H are prepared utilizing procedures previously described by starting with an appropriately substituted intermediate, or using standard methods known to those skilled in the art of organic chemistry for functional group interconversions.

Figure 9:
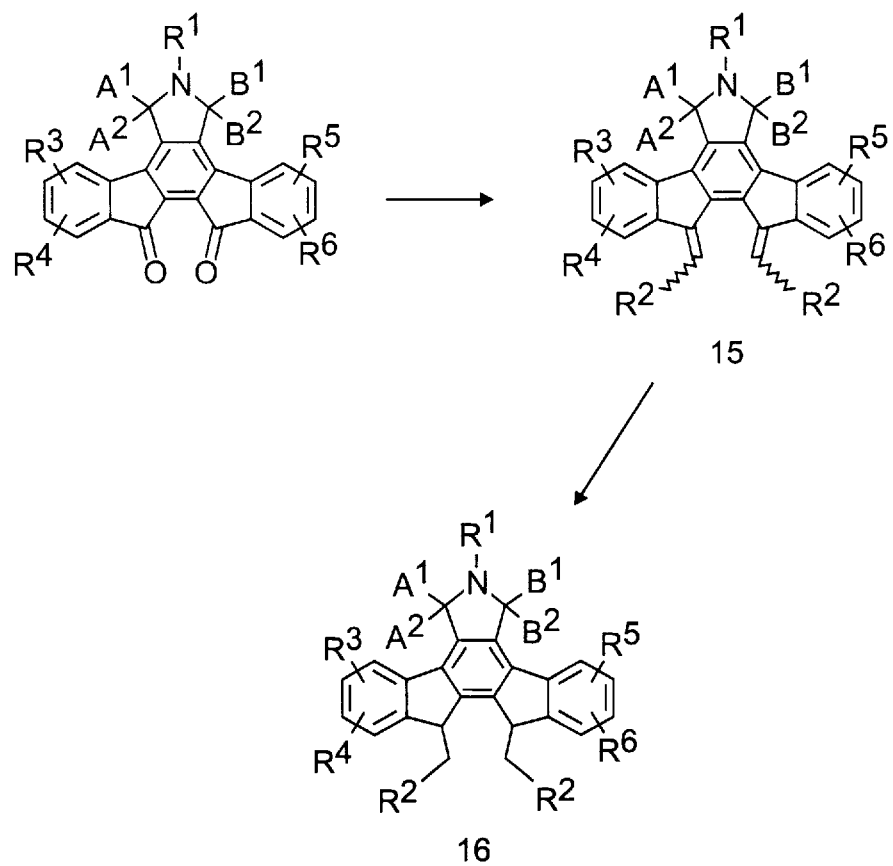
FIG. 9 shows a scheme for the synthesis of selected fused isoindolones using a Wittig reaction.
Figure 10:
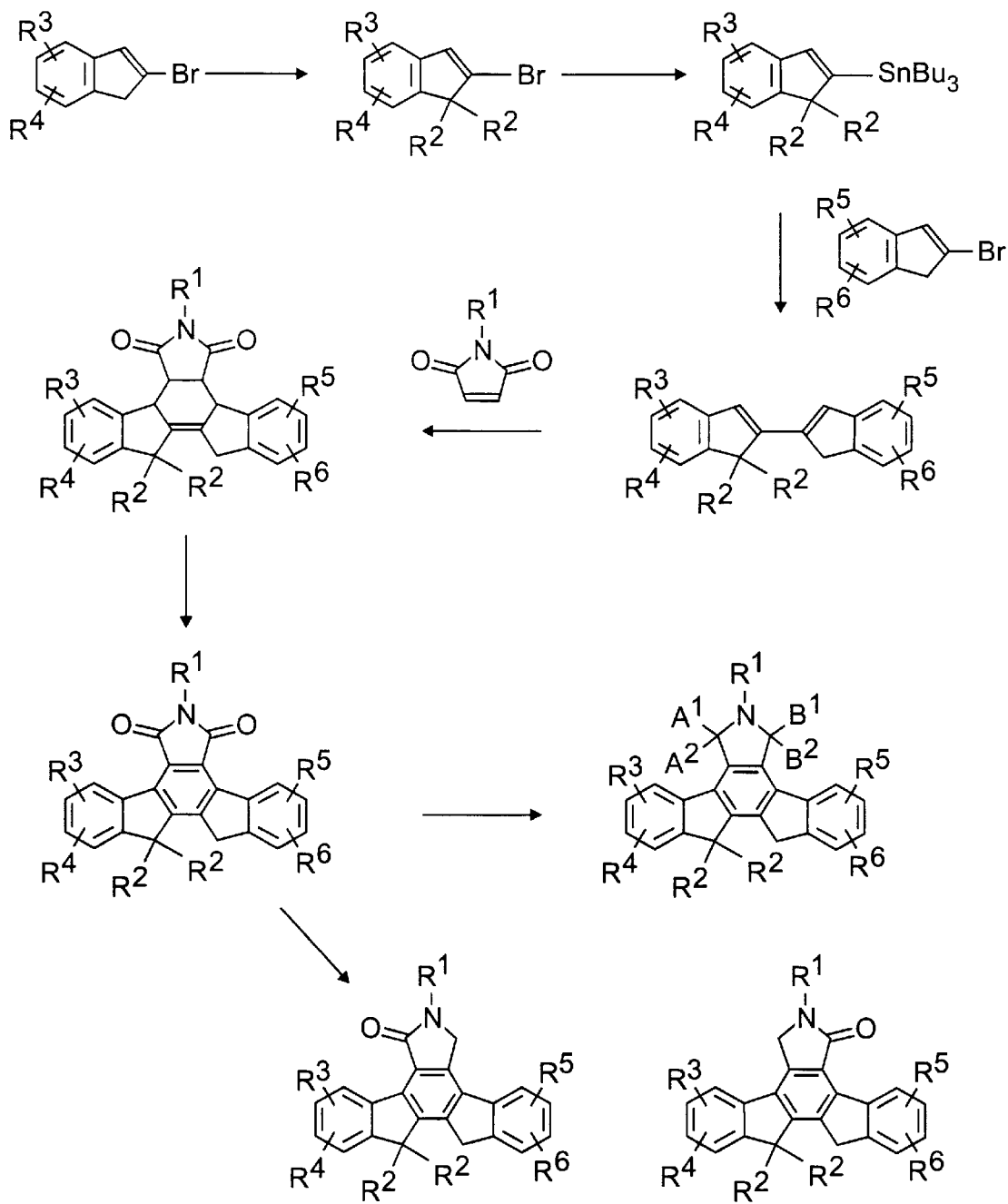
FIG. 10 shows a scheme for the synthesis of X-bis-alkylated fused isoindolones.

Derivatives with R$^2$ substitution where X group is a doubly bonded olefin (Formula II) may be formed from Wittig related olefination reactions on derivatives where X=(C=O, C=O or C=O, H) (FIG. 9), by those skilled in the art of organic synthesis. The resulting alkenes (15) may be reduced to compounds of the general structure (16) (FIG. 9). Derivatives where X=CH$_2$ may be readily alkylate by reaction with a strong base, such as BuLi, NaNH$_2$ or LiN(iPr)$_2$, followed by treatment with an appropriate electrophile (J. Med. Chem., 1992, 35, 3919; J. Org. Chem., 1991, 56, 4499) (FIG. 10).

Figure 11:
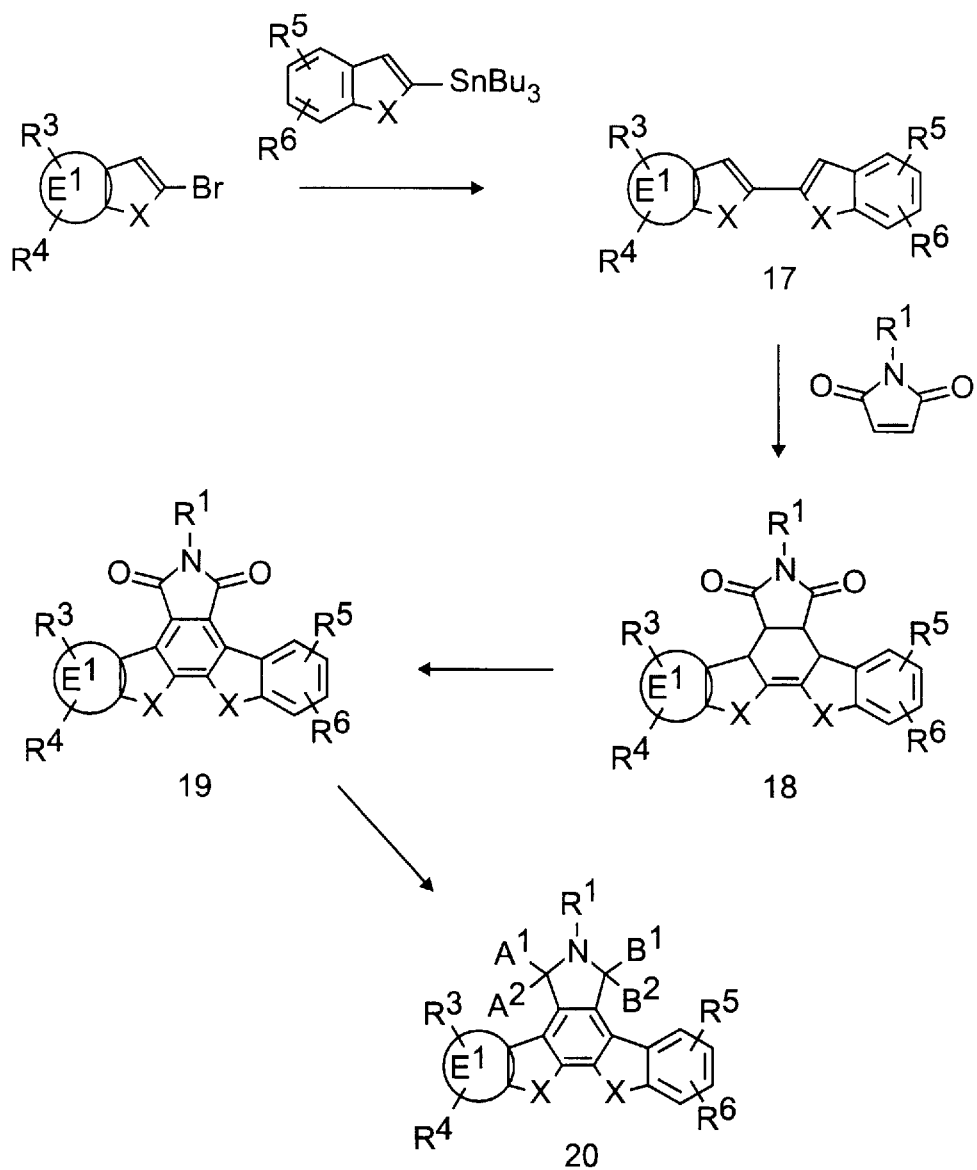
FIG. 11 shows a scheme for the synthesis of ring B heterocyclic fused isoindolones.
Figure 12:
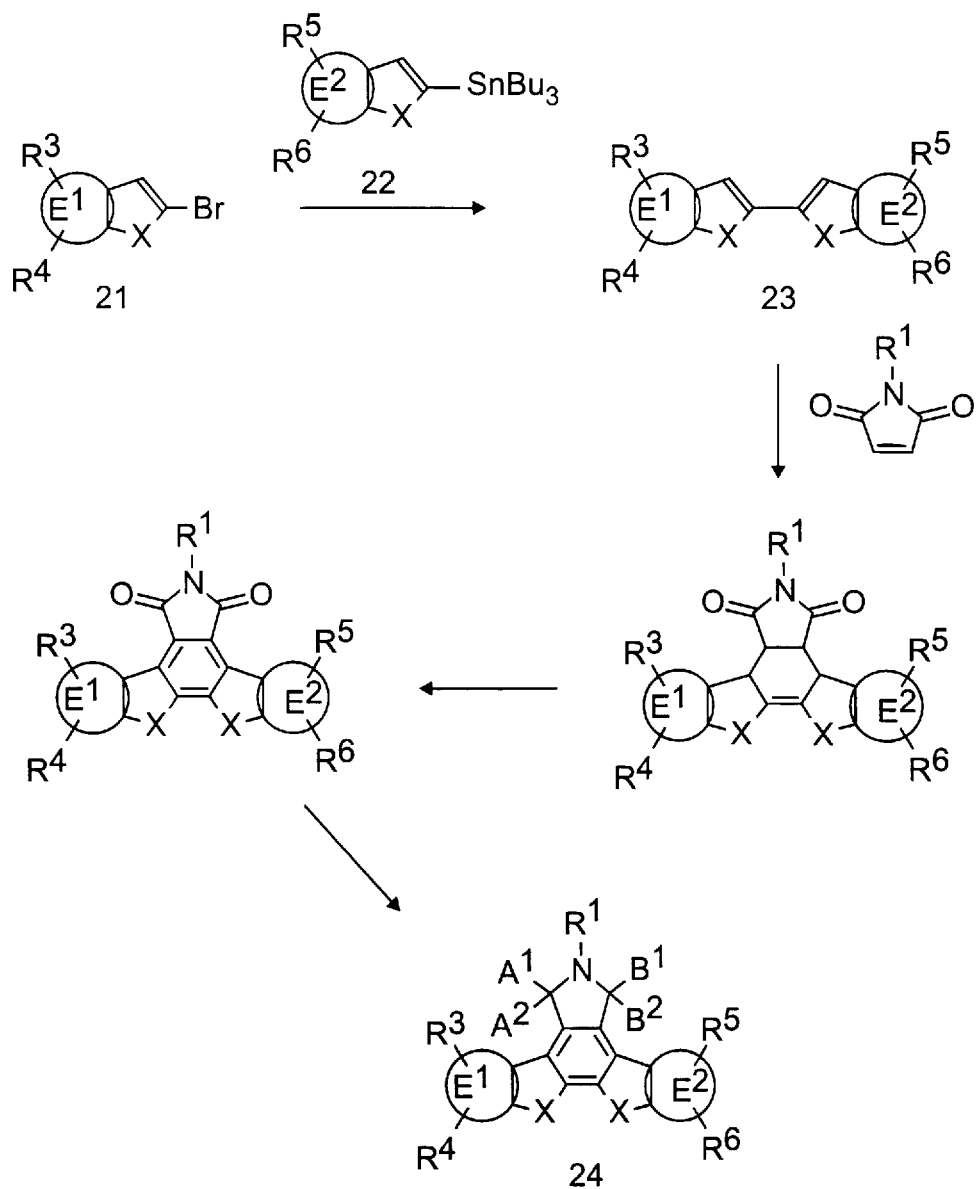
FIG. 12 shows a scheme for the synthesis of ring B and ring F bis-heterocyclic fused isoindolones.

Fused isoindolones of the Formula I in which the rings B and/or F may independently contain nitrogen, oxygen, or sulfur ring atoms, as defined above for E$^1$ and E$^2$, may be prepared by similar processes used to prepare the carbocyclic analogs (FIG. 11 and FIG. 12).

Preparation of derivatives in which ring B is a 6-membered nitrogen containing heterocyclic ring (nitrogen at any of 6 positions) are outlined in FIG. 11. Cycloaddition reactions of the compound of general structure 17 with maleimide would give compounds of the general structure 18. Dehydrogenation of intermediate 18 in a manner similar to preparation of Example IV(4) (FIG. 3) would give imide derivatives of the general structure 19 (FIG. 11). Lactam isomers of the general structure 20 may be prepared by the reaction of imide derivatives of the general structure 19 with reducing agents such as zinc amalgam-HCl, zinc amalgam in acetic acid, or hydride reducing agents such as lithium aluminum hydride. Regioisomers can be separated by standard processes such as recrystallization or chromatography, for example, column chromatography or HPLC. The imides are reduced to hydroxylactams where A$^1$, A$^2$ or B$^1$, B$^2$=H, OH, by hydride reducing agents such as borohydrides or aluminum hydrides.

Compounds in which ring B or F is a 5-membered ring containing oxygen or sulfur may be prepared starting with furyl-pyrroles or thieno-pyrroles, respectively, in place of indenes following the synthetic schemes outlined in FIG. 3 and 4. Ring fused furyl-pyrroles may be prepared using previously established literature procedures or modifications thereof (Coll. Czech. Chem. Commun. 53: 1770 (1988); Can. J. Chem. 56: 1429 (1978); C.R. Hebd. Seances Acad.

Sci., Ser. C 281: 793 (1975)). Ring fused thienyl-pyrroles may be prepared using previously established literature procedures or modifications thereof (Belgian patent specification BE 899925; Ind. J. Chem. 20B: 271 (1981); Can J. Chem. 56: 1429 (1978); Bull. Soc. Chim. Fr. 11-12 pt2: 2511 (1975); C.R. Hebd. Seances Acad. Sci., Ser. C 277: 1149 (1973)).

Alternatively, compounds in which ring B or F contains nitrogen ring atoms may be prepared starting with cycloalkanone-fused-pyridine derivatives (X=$C_1$–$C_3$ alkylene). The syntheses of cycloalkanone-pyridine derivatives have been described in the literature (J. Med. Chem. 36: 3381 (1993), Chem Ber., 1970, 103, 2403), and these compounds may be used directly to prepare intermediates of the general structure 21 or 22 (FIG. 12). Ring fused cycloalkyl- or cycloalkanone-pyridine derivatives may be converted to cyclic vinyl bromides by those skilled in the art of organic synthesis. The vinyl bromide intermediates would be suitable substrates to undergo the tin cross-coupling methodology described in FIG. 3 and FIG. 4.

Compounds in which ring F contains an oxygen atom may be prepared starting with furyl-fused cycloalkanones or cycloalkenyl derivatives (X=$C_1$–$C_3$ alkylene). Compounds in which ring F contains sulfur ring atoms may be prepared by starting with fused cycloalkenyl-thiophenes. Cycloalkyl ring-fused thienyl and furyl derivatives may be prepared using previously described literature procedures (Acta Chem. Scand. 25: 1287 (1971); J. Am. Chem. Soc. 103: 2760 (1981)) or modifications thereof. These intermediates can be converted to furyl- or thienyl-cyclopentanones or furyl- or thienyl-cyclopentenes. Alternatively the starting materials may be converted to the corresponding cyclic vinyl bromides by those skilled in the art of organic synthesis. The vinyl bromide intermediates may be used to give desired intermediates using the tin cross-coupling methodology described in FIG. 3 and FIG. 4.

Rings B and F may both be substituted by heteroatoms simultaneously as shown in FIG. 12. Intermediate 23 may be formed from a hetero atom-substituted B-ring tin intermediate 22, and an F-ring hetero atom-substituted cyclic vinyl bromide 21 (or triflate of the corresponding cyclic ketone intermediate). Imide and lactam derivatives containing hetero atoms in the B and F rings may be prepared by the methods shown in FIG. 3 and FIG. 4. Alternatively, Michael addition followed by palladium catalyzed ring closure described in FIG. 8 may be used to prepare imide derivatives of the general structure 20 (FIG. 11) and general structure 24 (FIG. 12). Reduction of the imides by the methods previously described would give lactam isomers.

Example IV(1): 2(Tributylstannyl) indene

To a round-bottom flask containing 2-bromoindene (1.64 g, 8.4 mmol) in 75 mL of $Et_3N$ was added palladium(II) acetate (304 mg, 11.4 mmol), tetrakis(triphenyl-phosphine) palladium(0), (775 mg, 0.7 mmol) and hexabutyl ditin (6.4 mL, 12.7 mmol). The reaction was heated to reflux and monitored by TLC (silica gel, EtOAc:hexane; 1:5). After 1 hour the starting material was consumed. The reaction was allowed to cool to room temperature, diluted with $CH_2Cl_2$, and was filtered through celite. The solvent was removed at reduced pressure and the compound was purified through a silica gel column (5% EtOAc-Hexane) to give 4.7 g of 2-tributylstannyl indene as a clear oil (contained traces of hexabutyl ditin). The compound was used as is for the next step. $^1$H NMR (300 MHz, $CDCl_3$): $\delta$ 0.9 (m, 15H), 1.2 (m, 6H), 1.6 (m, 6H), 3.5(s, 2H), 7.10 (s, 1H), 7.5–7.2 (m, 4H).

Example IV(2): 2,2'-Biindene

To a 100 mL round-bottom flask, fitted with a reflux condenser, was added 1.2 g (6.3 mmol) of 2-bromoindene, 3.4 g (8.4 mmol) of 2-tributylstannyl indene (Example IV(1)), and 70 mL of ethanol. To this mixture was added 442 mg (0.63 mmol) of bis(triphenylphosphine) palladium(II) chloride. The reaction was stirred at reflux for 16 h. The reaction was allowed to cool to rt, diluted with diethyl ether (50 mL), then filtered through a pad of alumina. The solvent was concentrated at reduced pressure and the product recrystallized from toluene to give 870 mg (60%) of 2,2'-biindene. mp=238° C. (lit. mp=238° C.; Chem. Ber., 1988, 121, 2195.) $^1$H NMR (300 MHz, $CDCl_3$): $\delta$ 3.73 (s, 4H), 6.93 (s, 2H), 7.30 (m, 8H). MS ($ES^+$) m/z=231 (M+1).

Example IV(3): 1a, 3a, 4, 7-Tetrahydroindenyl[2,3-c]indenyl[2,3-e]isoindol-1,3-dione A sealable borosilicate reaction tube was added 98 mg (0.4 mmol) of 2,2'-biindene (Example IV(2)), 43 mg (0.44 mmol) of maleimide, 5 mg of BHT, and 1 mL of $CH_2Cl_2$. The tube was sealed and the reaction was heated to 130° C. for 24 h. The reaction was allowed to cool to rt, and the solvent was concentrated at reduced pressure. The crude solid was purified via column chromotography (silica gel, 10–75% EtOAc-Hexane) to give 50 mg (38%) of a white solid, mp 244°–247° C. $^1$H NMR (300 MHz, $CDCl_3$): $\delta$ 3.68 (s, 4H), 3.80 (m, 2H), 4.00 (bs, 2H), 7.24 (m, 7H), 7.53 (d, J=7 Hz, 2H). MS ($ES^+$) m/z=328 (M+1).

Example IV(4): 1H-Indenyl[2,3-c]-1H-indenyl[2,3-e]isoindol-1,3-dione (Compound I-1)

A mixture of Example IV(3) (50 mg, 0.15 mmol) in toluene (4 mL) was added solid 2,3-dichloro-5,6-dicyano-1,4-benzquinone (79 mg, 0.35 mmol) in one portion. The reaction was heated under nitrogen at 65°–70° C. for 4 h. The solution was cooled in an ice bath and the solid material was collected by filtration. The crude precipitate was washed with cold methanol leaving a pale yellow solid (28 mg, 63 mp 244°–247° C. $^1$H NMR (300 MHz, $CDCl_3$): $\delta$ 9.17 (d, 4 Hz, 2H), 7.55 (m, 7H), 4.15 (s, 4H); MS (ES): m/z 346 (M+1).

Example IV(5): 1H-Indenyl[2,3-c]-1H-indenyl[2,3-e]-3H-isoindol-1-one (Compound I-2)

A zinc amalgam was prepared by suspension of 122 mg (1.9 mmol) of zinc dust in 1 mL of water and adding 35 mg (0.08 mmol) of $HgCl_2$ followed by 4 drops of cHCl. This mixture was stirred for 10 min. and the aqueous layer was decanted off. The amalgam was washed with water and then repeatedly with EtOH.

The above zinc amalgam was suspended in 5 mL of EtOH and Compound I-1 (Example IV(4)) (10 mg, 0.03 mmol) was added. A few drops of cHCl was added and the reaction was heated at reflux for 3 h. The yellow color disappeared during the first hour of heating. The reaction was allowed to cool to rt and the solution was concentrated at reduced pressure. The residue was dissolved in 10 mL of THF-EtOAc (1:1) and washed with saturated $NaHCO_3$ and NaCl solutions, then dried ($MgSO_4$). The drying agent was removed by filtration and the solvent concentrated at reduced pressure to give 8 mg (88%) of the lactam as a white solid, mp 256° C. $^1$H NMR (300 MHz, $CDCl_3$): $\delta$ 9.20 (d, 8 Hz, 1H), 7.50 (m, 6H), 6.24 (s, 1H), 4.83 (s, 2H), 4.05 (s, 2H), 3.95 (s, 2H); MS (ES): m/z 310 (M+1).

Example IV(6): 2,2'-Bibenzothiaphene

To a 2-neck round-bottom flask, fitted with a reflux condenser was added 3.3 g (15.6 mmol) of 2-bromobenzothiaphene, 7.3 g (17 mmol) 2-(tri-n-butyltin) benzo-thiaphene and 40 mL of toluene. To this mixture was added 360 mg (0.3 mmol) of tetrakis(triphenylphosphine) palladium(0) and 5 mg BHT. The reaction was heated at reflux for 16 hours. After cooling to room temperature the solvent was removed under vacuum, the reaction was dissolved in DMF and filtered through celite. The solvent was removed under vacuum and the solid was triturated with hexanes to give 3.58 g (13.4 mmol, 85% yield) of 2,2'bibenzothiaphene as a silver, black solid. mp=260°–262° C. $^1$H NMR (300 MHz, DMSO d$_6$) δ 7.98 (m, 2H), 7.62 (s, 1H), 7.36 (m, 2H), 7.25 (s, 1H).

Example IV(7): 3,4-Carboethoxybenzothienyl [1,2-a] dibenzothiaphene

In a sealable glass tube was placed 1.02 g (3.8 mmol) of 2,2'-bibenzothiaphene, 3.1 mL (19 mmol) of diethyl acetylenedicarboxylate, and 5 mg BHT. The reaction vessel was sealed under N$_2$ and heated at 190° C. The reaction was allowed to go for 24 hours. After allowing the reaction vessel to cool, the contents were transferred to a round-bottom using CHCl$_3$ and the solvent was removed under vacuum. The solid was taken up in diethylether and filtered giving 468 mg (1.07 mmol, 28%) of 3,4-carboethoxybenzothienyl [1,2-a]dibenzothiaphene as a pale yellow solid, mp 206°–207° C. A second crystallization afforded 280 mg more material for a total yield of 45%. $^1$H NMR (300 MHz, DMSO $_6$) δ 8.27 (d, 7.4 Hz, 2H), 8.05 (d, 7.9 Hz, 2H), 7.65 (m, 4H), 4.57 (q, 7.1 Hz, 4H), 1.38 (t, 7.1 Hz, 6H).

Example IV(8): Benzothienyl[4,5-a]benzothienyl [6,7-a] isobenzofuran-1,3-dione

A round-bottomed flask was charged with 500 mg (1.15 mmol) of 3,4-carboethoxybenzothienyl[1,2-a] dibenzothiaphene and 50 mL of DMF. To this mixture was added 124 mg (2.5 mmol) of sodium cyanide and 476 mg (2.5 mmol) of lithium iodide trihydrate in solid form. The reaction was heated to 150° C. and followed by TLC. More NaCN/LiI was added as time progressed. A total of 4 equivalents each NaCN and LiI were added over a reaction time of 36 hours, at which time the starting material was totally consumed. The reaction mixture was cooled to room temperature and poured over cold (0° C.) aqueous HCl. The mixture was filtered and washed with water. The resultant solid was dried under vacuum.

The above crude solid was then placed in a round-bottomed flask and 50 mL of acetic anhydride was added. The reaction mixture was then heated to reflux. After 4 hours at reflux the reaction was complete by TLC (new spot at R$_f$ 0.65 in 1:1 EtOAc/Hexanes). The solvent was removed and the crude oil was purified via flash chromatography to give a bright yellow-orange solid. This solid was triturated with diethyl ether to give 160 mg (0.44 mmol, 40% yield) of benzothienyl[4,5-a]benzothienyl[6,7-a]isobenzofuran-1,3-dione as a bright yellow solid, mp>300° C. $^1$H NMR (300 MHz, DMSO d$_6$) δ 9.54 (dd, 5.2 Hz, 2.5 Hz, 2H), 8.34 (dd, 4.0 Hz, 3.3 Hz, 2H), 7.73 (m, 4H).

Example IV(9): Benzothieno[2,3-c]benzothieno[2,3-e] isoindol-1,3-dione (Compound I-3)

Benzothienyl[4,5-a]benzothienyl[6,7-a]isobenzofuran-1,3-dione (75 mg, 0.2 mmol) was dissolved in 3 mL DMF. To this mixture was added 4.4 mL (20.8 mmol) of 1,1,1,3,3,3-hexamethyldisilazane followed by 30 μL (1 mmol) methanol. The suspension became clear after approximately 15 minutes. The TLC after one hour showed nearly complete consumption of starting material. The reaction was allowed to stir overnight for a total reaction time of 18 hours. Solvent was removed to give 65 mg (0.18 mmol, 80% yield) of benzothieno[2,3-c]benzothieno[2,3-e]isoindol-1,3-dione as a yellow solid, mp>300° C. $^1$H NMR (300 MHz, DMSO d$_6$) δ 9.8 (dd, 5.0 Hz, 4.1 Hz, 2H), 8.25 (dd, 4.9 Hz, 4.1 Hz, 2H), 7.70 (m, 4H).

Example IV(10): Benzothieno[2,3-c]benzothieno[2,3-e] isoindol-1-one (Compound I-4)

To a 10 mL ethanol suspension of Zn amalgam (3 eq.) was added 68 mg (0.18 mmol) of the benzothieno[2,3-c] benzothieno[2,3-e]isoindol-1,3-dione as a solution in 10 mL acetic acid. The reaction was heated to reflux after the addition of 5 mL of concentrated HCl. After refluxing overnight the reaction became clear and slightly tan. The reaction was cooled and decanted off of the mercury layer. After removing most of the solvent the mixture was diluted with ethyl acetate and washed two times with saturated NaHCO$_3$. The organic layer was dried over MgSO$_4$, filtered, and solvent was removed. The crude reaction mixture was purified via column chromatography to give 65 mg (0.18 mmol, 100% yield) of benzothieno[2,3-c]benzothieno[2,3-e]isoindol-1-one as a tan solid, mp 225°–226° C. $^1$H NMR (300 MHz, DMSO d$_6$) δ 10.17 (dd, 6.4 Hz, 2.7 Hz, 1H), 8.22 (s, 1H), 8.21 (dd, 4.1 Hz, 3.7 Hz, 2H), 8.11 (dd, 6.5 Hz, 2.2 Hz, 1H), 7.63 (t, 3.7 Hz, 2H), 7.55 (t, 3.7 Hz, 2H), 5.19 (s, 2H).

Example IV(11): 2-(2'-Indenyl)benzothiaphene

To a 2-neck round-bottom flask, fitted with a reflux condenser was added 2 g (13.3 mmol) of 2-bromoindene, 5.1 g (11.9 mmol) 2-(tri-n-butyltin)benzothiaphene and 50 mL of toluene. To this mixture was added 1 g (1.5 mmol) of bis(triphenylphosphine) palladium(II) dichloride and 5 mg BHT. The reaction was heated at reflux for 16 hours. After allowing to cool the solvent was removed, reaction was taken up in DMF/THF and filtered through celite. The solvent was removed and the solid was triturated with hexanes to give 1.4 g (5.6 mmol, 47% yield) of 2-(2'-indenyl)benzothiaphene as an orange solid. mp=260°–265° C. $^1$H NMR (DMSO d$_6$) δ 7.82 (m, 4H), 7.61 (s, 1H), 7.35 (m, 5H), 3.97 (s, 2H).

Example IV(12): 3,4-Carboethoxyiendenyl[1,2-a] dibenzothiaphene

In a sealable glass tube was placed 480 mg (3.95 mmol) of 2-(2'-indenyl)benzothiaphene, 3.2 mL (19 mmol) of diethyl acetylenedicarboxylate, and 10 mg BHT. The reaction vessel was sealed under N$_2$ and heated at 190° C. The reaction was allowed to go for 24 hours. After allowing the vessel to cool the contents were transferred to a round-bottom using CHCl$_3$ and solvent was removed. The crude material was passed through a silica column, collecting the top fractions. This solid was taken up in diethylether and filtered giving 538 mg (1.29 mmol, 23%) of 3,4-carboethoxyiendenyl-[1,2-a]dibenzothiaphene as a pale orange solid, mp 186° C. $^1$H NMR (300 MHz, DMSO d$_6$) δ 8.15 (d, 7.4 Hz, 1H), 7.95 (d, 7.4 Hz, 1H), 7.71 (m, 2H), 7.56 (m, 2H), 7.41 (m, 2H), 4.50 (q, 7.0 Hz, 4H), 4.22 (s, 2H), 1.33 (t, 7.0 Hz, 6H).

Example IV(13): Indenyl[4,5-a]benzothienyl[6,7-a] isobenzofuran-1,3-dione

A round-bottomed flask was charged with 250 mg (0.6 mmol) of 3,4-carboethoxyendenyl[1,2-a]dibenzothiaphene and 10 mL of pyridine. To this mixture was added 677 mg (3.6 mmol) of lithium iodide trihydrate. The reaction was heated to 115° C. and followed by TLC. More LiI was added as time progressed. A total of 5 equivalents LiI was added over a reaction time of 36 hours, at which time the starting material was totally consumed. The reaction mixture was cooled to room temperature and poured over cold (0° C.) aqueous HCl. The mixture was filtered and washed with water. The resultant solid was dried under vacuum.

The above crude solid was then placed in a round-bottomed flask and 50 mL of acetic anhydride was added. The reaction mixture was then heated to reflux. After 4 hours at reflux the reaction was complete by TLC (new spot at R$_f$ 0.6 in 1:1 EtOAc/Hexanes). The solvent was removed and the crude oil was purified via flash chromotography to give a bright yellow-orange solid. This solid was triturated with diethyl ether to give 160 mg (0.44 mmol, 40% yield) of indenyl[4,5-a]benzothienyl[6,7-a]isobenzofuran-1,3-dione as a bright yellow solid, mp>300° C. $^1$H NMR (300 MHz, DMSO $d_6$) δ 9.65 (d, J=7.2 Hz, 1H), 8.76 (d, J=7.6 Hz, 1H), 8.15 (s, J=7.4 Hz, 1H), 7.78–7.38 (m,5H), 4.97 (s, 2H).

Example IV(14): Indenyl[2,3-c]benzothienyl[2,3-e]isoindol-1,3-dione (Compound I-5)

Indenyl[4,5-a]benzothienyl[6,7-a]isobenzofuran-1,3-dione (120 mg, 0.35 mmol) was dissolved in 3 mL DMF. To this mixture was added 7.4 mL (35 mmol) of 1,1,1,3,3,3-hexamethyldisilazane followed by 50 μL (1 mmol) methanol. The suspension became clear after approximately 15 minutes. The TLC after one hour showed nearly complete consumption of starting material. The reaction was allowed to stir overnight for a total reaction time of 18 hours. Solvent was removed to give 35 mg (0.18 mmol, 30% yield) of indenyl[2,3-c]benzothienyl[2,3-e]isoindol-1,3-dione as a orange solid, $^1$H NMR (300 MHz, DMSO $d_6$) δ 12.72 (s, 1H), 9.84 (d, J=8.3 Hz, 1H), 8.14 (d, J=6.4 Hz, 1H), 8.07 (d, J=7.5 Hz, 1H), 7.82–7.28 (m, 5H), 5.03 (s, 2H), MS (APcI) 342 (M+H).

Example IV(15): Indenyl[2,3-c]benzothienyl[2,3-e]isoindol-1 and 3-one (Compound I-6)

To a 2 mL ethanol suspension of Zn amalgam (3 eq.) was added 10 mg (0.3 mmol) of the indenyl[2,3-c]thianaphtheno[2,3-e]isoindol-1,3-dione as a solution in 10 mL acetic acid. The reaction was heated to reflux after the addition of 1 mL of concentrated HCl. After refluxing 3 h the reaction became clear and slightly tan. The reaction was cooled and decanted off of the mercury layer. After removing most of the solvent the mixture was diluted with ethyl acetate and washed two times with saturated NaHCO$_3$. The organic layer was dried over MgSO$_4$, filtered, and solvent was removed to give the compound as a mixture of indenyl[2,3-c]thianaphtheno[2,3-e]isoindol-1-one as a tan solid, MS (APcI) 329 (M+H).

While the invention has been described in considerable detail, the invention disclosed herein is not to be limited by the actual description but is to be afforded the full scope of any appended claims and all equivalents thereto.

We claim:

1. A compound whose chemical structure is:

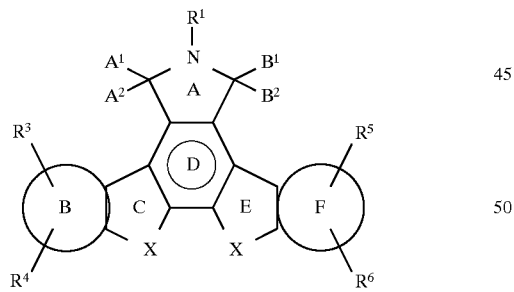

wherein:
ring B and ring F are independently selected from the group consisting of:
(a) a 6-membered carbocyclic aromatic ring; and
(b) a 5-membered carbocyclic aromatic ring;

$R^1$ is selected from the group consisting of H; alkyl of 1–4 carbons; aryl; arylalkyl; heteroaryl; heteroarylalkyl; COR$^9$, where R$^9$ is selected from the group consisting of alkyl of 1–4 carbons, aryl and heteroaryl; —OR$^{10}$, where R$^{10}$ is selected from the group consisting of H and alkyl of 1–4 carbons; —CONH$_2$, —NR$^7$R$^8$, —(CH$_2$)$_n$NR$^7$R$^8$, and —O(CH$_2$)$_n$NR$^7$R$^8$, where n is 1–4, and (a) R$^7$ and R$^8$ independently are selected from the group consisting of H and alkyl of 1–4 carbons; or
(b) R$^7$ and R$^8$ together form a linking group of the formula —(CH$_2$)$_2$—X$^1$—(CH$_2$)$_2$—, where X$^1$ is selected from the group consisting of —O—, —S—, and —CH$_2$—;

A$^1$ and A$^2$, pairwise, are selected from the group consisting of: H, H; H, —OR$^{11}$, where R$^{11}$ is H, alkyl of 1–4 carbons, aryl of 6–10 carbons, or heteroaryl; H, —SR$^{11}$; H, —N(R$^{11}$)$_2$; =O; =S; and =NR$^{11}$, where A$^1$ and A$^2$ together can represent a double-bonded atom;

B$^1$ and B$^2$, pairwise, are selected from the group consisting of: H, H; H, —OR$^{11}$; H, —SR$^{11}$; H, —N(R$^{11}$)$_2$; =O; =S; and =NR$^{11}$, where B$^1$ and B$^2$ together can represent a double-bonded atom; with the proviso that at least one of the pairs A$^1$ and A$^2$, and B$^1$ and B$^2$, is =O;

X, at each position, is independently selected from the group consisting of:
(a) an unsubstituted alkylene of 1–3 carbons;
(b) an alkylene of 1–3 carbons substituted with R$^2$, where R$^2$ is selected from the group consisting of: OR$^{10}$; —SR$^{10}$; R$^{15}$, where R$^{15}$ is alkyl of 1–4 carbons; phenyl, naphthyl; arylalkyl of 7–14 carbons; H; —SO$_2$R$^9$; —CO$_2$R$^9$, —COR$^9$, alkyl, alkenyl, or alkynyl of 1–8 carbons; where
(i) each alkyl, alkenyl, or alkynyl of 1–8 carbons is unsubstituted; or
(ii) each alkyl, alkenyl, or alkynyl of 1–8 carbons is substituted with a substituent selected from the group consisting of 1–3 aryl of 6–10 carbons; heteroaryl; F; Cl; Br; I; —CN; —NO$_2$; OH; —OR$^9$; —O(CH$_2$)$_n$NR$^7$R$^8$, where n is 1–4; —OCOR$^9$; —OCONHR$^9$; O-tetrahydropyranyl; NH$_2$; —NR$^7$R$^8$; —NR$^{10}$COR$^9$; —NR$^{10}$CO$_2$R$^9$; —NR$^{10}$CONR$^7$R$^8$; —NHC(=NH)NH$_2$; —NR$^{10}$SO$_2$R$^9$; —S(O)$_y$R$^{11}$, where y is 1 or 2; —SR$^{11}$; —CO$_2$R$^9$; —CONR$^7$R$^8$; —CHO; COR$^9$; —CH$_2$OR$^7$; —CH=NNR$^{11}$R$^{12}$, where R$^{12}$ is selected from the group consisting of H, alkyl of 1–4 carbons, aryl of 6–10 carbons, and heteroaryl; —CH=NOR$^{11}$; —CH=NR$^9$; —CH=NNHCH(N=NH)NH$_2$; —SO$_2$NR$^{12}$R$^{13}$, where R$^{13}$ is selected from the group consisting of H, alkyl of 1–4 carbons, aryl of 6–10 carbons, and heteroaryl, or R$^{12}$ and R$^{13}$ together form a linking group consisting of —(CH$_2$)$_2$—X$^1$—(CH$_2$)$_2$—, wherein X$^1$ is —O—, —S—, or —CH$_2$—; —PO(OR$^{11}$)$_2$, —OR$^{14}$, where R$^{14}$ is the residue of an amino acid after the hydroxyl group of the carboxyl group is removed; and
(c) a functional group selected from the group consisting of —CH=CH—; —CHOH—CHOH—; —O—; —S—; —S(=O)—; —S(=O)$_2$—; —C(R$^{10}$)$_2$—; —C=C(R$^2$)$_2$; —C(=O)—; —C(=NOR$^{11}$)—; —C(OR$^{11}$)(R$^{11}$)—; —C(=O)CH(R$^{15}$)—; —CH(R$^{15}$)C(=O)—; —C(=NOR$^{11}$)CH(R$^{15}$)—; —CH(R$^{15}$)C(=NOR$^{11}$)—; CONR$^{15}$; NR$^{15}$CO; —CH$_2$Z—; —ZCH$_2$—, and —CH$_2$ZCH$_2$—, where Z is —O—; —S—; —C(=NOR$^{11}$), or —NR$^{11}$;

R$^3$, R$^4$, R$^5$ and R$^6$ each is independently selected from the group consisting of: H; aryl; heteroaryl; F; Cl; Br; I; —CN; CF$_3$; —NO$_2$; OH; —OR$^9$; —O(CH$_2$)$_n$NR$^7$R$^8$; —OCOR$^9$; —OCONHR$^9$; NH$_2$; —CH$_2$OH; —CH$_2$OR$^{14}$; —NR$^7$R$^8$; —NR$^{10}$COR$^9$; —NR$^{10}$CONR$^7$R$^8$; —SR$^{11}$; —S(O)$_y$R$^{11}$, where y is 1 or 2; —CO$_2$R$^9$; —COR$^9$; —CONR$^7$R$^8$; —CHO; —CH=NOR$^{11}$; —CH=NR$^9$; —CH=NNR$^{11}$R$^{12}$; —(CH$_2$)$_n$SR$^9$, where n is 1–4; —(CH$_2$)$_n$S(O)$_y$R$^9$; —CH$_2$SR$^{15}$, where R$^{15}$ is alkyl of 1–4 carbons; —CH$_2$S(O)$_y$R$^{14}$; —(CH$_2$)$_n$NR$^7$R$^8$; —(CH$_2$)$_n$NHR$^{14}$; alkyl, alkenyl, alkynyl of 1–8 carbons; where
(a) each alkyl, alkenyl, or alkynyl of 1–8 carbons is unsubstituted; or
(b) each alkyl, alkenyl, or alkynyl of 1–8 carbons is substituted with 1–3 aryl of 6–10 carbons; heteroaryl; F; Cl; Br; I; —CN; —NO$_2$; OH; —OR$^9$; —O(CH$_2$)$_n$NR$^7$R$^8$; —OCOR$^9$; —OCONHR$^9$; O-tetrahydropyranyl; NH$_2$; —NR$^7$R$^8$; —NR$^{10}$COR$^9$; —NR$^{10}$CO$_2$R$^9$; —NR$^{10}$CONR$^7$R$^8$; —NHC(=NH)NH$_2$; —NR$^{10}$SO$_2$R$^9$; —S(O)$_y$R$^{11}$, and y is 1 or 2; —SR$^{11}$; —CO$_2$R$^9$; —CONR$^7$R$^8$; —CHO; COR$^9$; —CH$_2$OR$^7$; —CH=NNR$^{11}$R$^{12}$; —CH=NOR$^{11}$; —CH=NR$^9$; —CH=NNHCH(N=NH)NH$_2$; —SO$_2$NR$^{12}$R$^{13}$; —PO(OR$^{11}$)$_2$; OR$^{14}$; or a monosaccharide of 5–7 carbons where each hydroxyl group of the monosaccharide independently is either unsubstituted or is replaced by H, alkyl of 1–4 carbons, alkylcarbonyloxy of 2–5 carbons or alkoxy of 1–4 carbons.

2. The compound of claim 1, wherein the chemical structure is:

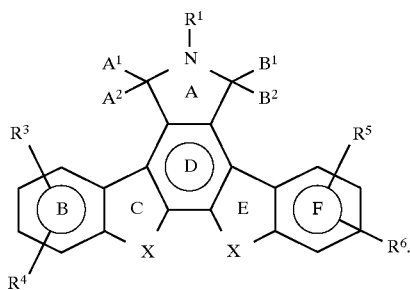

3. The compound of claim 2, wherein A$^1$ and A$^2$ are selected pairwise from the group consisting of H, H; H, OH; and =O; and B$^1$ and B$^2$ are selected pairwise from the group consisting of H, H; H, OH; and =O; provided that A$^1$ and A$^2$, or B$^1$ and B$^2$, are =O.

4. The compound of claim 2, wherein R$^1$ is H.

5. The compound of claim 2, wherein R$^1$ is COR$^9$, and R$^9$ is selected from the group consisting of phenyl and naphthyl.

6. The compound of claim 2, wherein X, at either position, or both positions, is an unsubstituted alkylene of 1–3 carbons.

7. The compound of claim 2, wherein X, at either position, or both positions, is selected from the group consisting of —O— and —S—.

8. The compound of claim 2, wherein X has an R$^2$ substituent and R$^2$ is —OR$^{10}$.

9. The compound of claim 2, wherein X has an R$^2$ substituent, and R$^2$ is benzyl.

10. The compound of claim 2, wherein X has an R$^2$ substituent and R$^2$ is selected from the group consisting of alkyl of 1–4 carbons, alkenyl of 1–4 carbons, and alkynyl of 1–4 carbons.

11. The compound of claim 2, wherein X has an R$^2$ substituent, and R$^2$ is selected from the group consisting of substituted alkyl of 1–8 carbons, substituted alkenyl of 1–8 carbons, and substituted alkynyl of 1–8 carbons, and R$^2$ has a substituent selected from the group consisting of phenyl and naphthyl.

12. The compound of claim 2, wherein X has an R$^2$ substituent, R$^2$ is —S(O)$_y$R$^{11}$, y is 1 or 2, and R$^{11}$ is phenyl or naphthyl.

13. The compound of claim 2, wherein X has an R$^2$ substituent, R$^2$ has a substituent that is —CH=NNR$^{11}$R$^{12}$ or —SO$_2$NR$^{12}$R$^{13}$, and R$^{12}$ or R$^{13}$ is selected from the group consisting of phenyl and naphthyl.

14. The compound of claim 2, wherein X has an R$^2$ substituent and R$^{12}$ and R$^{13}$ together represent a linking group.

15. The compound of claim 14, wherein said linking group is —(CH$_2$)$_2$—X$^1$—(CH$_2$)$_2$—, where X$^1$ is selected from the group consisting of —O—; —S—; and —CH$_2$—.

16. The compound of claim 2, wherein R$^3$, R$^4$, R$^5$ and R$^6$ are H.

17. The compound of claim 2, wherein at least one of R$^3$, R$^4$, R$^5$ and R$^6$ is selected from the group consisting of phenyl and naphthyl, with the proviso that either R$^3$ or R$^4$ is H, and either R$^5$ or R$^6$ is H.

18. The compound of claim 2, wherein at least one of R$^3$, R$^4$, R$^5$ and R$^6$ is selected from the group consisting of alkyl of 1–4 carbons, alkenyl of 1–4 carbons, and alkynyl of 1–4 carbons, with the proviso that either R$^3$ or R$^4$ is H, and either R$^5$ or R$^6$ is H.

* * * * *